United States Patent
Chen et al.

(10) Patent No.: US 8,502,544 B1
(45) Date of Patent: Aug. 6, 2013

(54) METHOD FOR TESTING MASK ARTICLES

(75) Inventors: Ming-Chih Chen, Hsinchu (TW);
Hsiang-Jen Yang, Hsinchu (TW);
Chen-Rui Tseng, Hsinchu (TW)

(73) Assignee: Taiwan Mask Corporation, Hsinchu (TW)

(*) Notice: Subject to any disclaimer, the term of this patent is extended or adjusted under 35 U.S.C. 154(b) by 0 days.

(21) Appl. No.: 13/549,452

(22) Filed: Jul. 14, 2012

Related U.S. Application Data

(60) Provisional application No. 61/646,447, filed on May 14, 2012.

(51) Int. Cl.
*H01H 31/12* (2006.01)
*G01N 27/00* (2006.01)
*G01R 31/26* (2006.01)
*G01V 8/00* (2006.01)

(52) U.S. Cl.
USPC .... 324/551; 324/557; 324/760.01; 250/559.4

(58) Field of Classification Search
USPC ............. 324/509, 525, 541, 544, 548, 551, 324/557, 760.01–760.02, 762.01; 250/559.4–559.45
See application file for complete search history.

(56) References Cited

U.S. PATENT DOCUMENTS

| | | | |
|---|---|---|---|
| 4,398,343 A * | 8/1983 | Yamazaki | 438/88 |
| 5,225,785 A * | 7/1993 | Mayer et al. | 324/671 |
| 6,181,139 B1 * | 1/2001 | Joergensen et al. | 324/455 |
| 6,184,691 B1 * | 2/2001 | Prough | 324/551 |
| 6,563,334 B2 * | 5/2003 | Tsuru | 324/762.01 |
| 6,707,055 B2 * | 3/2004 | Vargas | 250/559.4 |
| 6,784,446 B1 * | 8/2004 | Phan et al. | 250/559.4 |
| 6,919,957 B2 * | 7/2005 | Nikoonahad et al. | 356/237.2 |
| 7,583,094 B2 * | 9/2009 | Hiroki | 324/754.23 |
| 7,688,083 B2 * | 3/2010 | De Vries et al. | 324/699 |
| 8,289,031 B1 * | 10/2012 | Rao | 324/551 |
| 2002/0182760 A1 * | 12/2002 | Wack et al. | 438/14 |
| 2005/0213083 A1 | 9/2005 | Sekine et al. | |
| 2005/0289488 A1 | 12/2005 | Chou et al. | |
| 2010/0142800 A1 | 6/2010 | Tung-Sing Pak et al. | |
| 2010/0149505 A1 | 6/2010 | Sewell et al. | |
| 2010/0201376 A1 * | 8/2010 | Ouyang et al. | 324/551 |

* cited by examiner

*Primary Examiner* — Joshua Benitez-Rosario
(74) *Attorney, Agent, or Firm* — Sinorica, LLC; Ming Chow

(57) ABSTRACT

A method for testing a mask article includes the steps of electrically connecting the mask article to an electrical sensor, applying a bias voltage to a plurality of testing sites of the mask article with a conductor, measuring at least one current distribution of the testing sites with the electrical sensor, and determining the quality of the mask article by taking the at least one current distribution into consideration.

25 Claims, 27 Drawing Sheets

METHOD FOR TESTING MASK ARTICLES

The current application claims a priority to U.S. 61/646,447 filed on May 14, 2012.

BACKGROUND

1. Technical Field

The present disclosure relates to a method for testing a mask article, and more particularly, to a method for testing a mask article by applying an electrical bias across the mask article and measuring the corresponding current distribution of the mask article.

2. Description of Related Arts

Semiconductor photolithography processes utilize masks for patterning Conventionally, mask designers manufacture masks according to integrated circuit (IC) designs in semiconductor industries or thin film transistor (TFT) designs for liquid crystal display (LCD) and color filter (CF) designs in photoelectronic industries or printed circuit board (PCB) designs obtained from IC, TFT, LCD, CF, PCB designers/clients. After finishing the masks, the mask designers will provide the IC, TFT, LCD, CF, PCB designers and/or clients with defect maps for showing the locations of mask defects on a corresponding wafer or a photoelectronic substrate (e.g. glass substrate) onto which mask patterns of the masks will be transferred.

A mask defect on a mask is anything that is different from a desired mask pattern and that occurs during the mask manufacturing process. Typically, the above defects on the mask can be inspected, for instance, by scanning the surface of the finished mask with a high resolution microscope or an inspection machine and capturing images of the mask. The next step is determining whether or not the inspected mask is good enough for use in the lithography process. This step can be performed by a skilled-inspection engineer, or by fabrication workers possibly with the aid of inspection software. If there are no defects, or defects are discovered but determined to be within tolerances set by the manufacturer or end-user, then the mask is passed and used to expose a wafer or photoelectronic substrate. If defects are discovered and fall outside tolerances, then the mask fails the inspection, and a decision must be made as to whether the mask may be cleaned and/or repaired to correct the defects, or whether the defects are so severe that a new mask must be manufactured.

As a result of the continuous progression of smaller pattern design, even very small defects in the mask or the mask blanks can negatively affect production yields. For example, the major challenge for Extreme Ultraviolet lithography (EUVL) is how to provide a defect-free mask blank; i.e., how to detect the nano-scale defects on the mask blank. However, the conventional defect detection system cannot meet the precision requirements resulting from the continuous progression of smaller pattern design. Hence, there is a need for a defect detection system that addresses the inefficiency arising from the existing technology.

SUMMARY

One aspect of the present disclosure provides a method for testing a mask article by applying an electrical bias across the mask article and measuring the corresponding current distribution of the mask article.

A method for testing a mask article according to one embodiment of the present disclosure comprises the steps of electrically connecting the mask article to an electrical sensor, applying a bias voltage to a plurality of testing sites of the mask article with a conductor, measuring at least one current distribution of the testing sites with the electrical sensor, and determining the quality of the mask article by taking the at least one current distribution into consideration.

A method for testing a mask article according to another embodiment of the present disclosure comprises the steps of applying a bias voltage to the mask article, electrically connecting a conductor to an electrical sensor, contacting a plurality of testing sites of the mask article with the conductor, measuring at least one current distribution of the testing sites with the electrical sensor through the conductor, and determining the quality of the mask article by taking the at least one current distribution into consideration.

The foregoing is a broad outline of the features and technical advantages of the present disclosure in order that the detailed description of the following may be better understood. It should be noted that additional features and advantages of the disclosure will be described hereinafter, which form the subject of the claims of the disclosure. It should be appreciated by those skilled in the art that the conception and specific embodiment disclosed may be readily utilized as a basis for modifying or designing other structures or processes for carrying out the same purposes of the present disclosure. It should also be realized by those skilled in the art that such equivalent constructions do not depart from the spirit and scope of the disclosure as set forth in the appended claims.

BRIEF DESCRIPTION OF THE DRAWINGS

A more complete understanding of the present disclosure may be derived by referring to the detailed description and claims when considered in connection with the Figures, wherein like reference numbers refer to similar elements throughout the Figures as follows:

DETAILED DESCRIPTION

The following description of the disclosure accompanies drawings, which are incorporated in and constitute a part of this specification, and illustrate embodiments of the disclosure, but the disclosure is not limited to the embodiments. In addition, the following embodiments can be properly integrated to complete another embodiment.

The present disclosure is directed to a method for testing a mask article. In order to make the present disclosure completely comprehensible, detailed steps and structures are provided in the following description. Obviously, implementation of the present disclosure does not limit special details known by persons skilled in the art. In addition, known structures and steps are not described in detail, so as not to limit the present disclosure unnecessarily. Preferred embodiments of the present disclosure will be described below in detail. However, in addition to the detailed description, the present disclosure may also be widely implemented in other embodiments. The scope of the present disclosure is not limited to the detailed description, and is defined by the claims.

Figure 1:
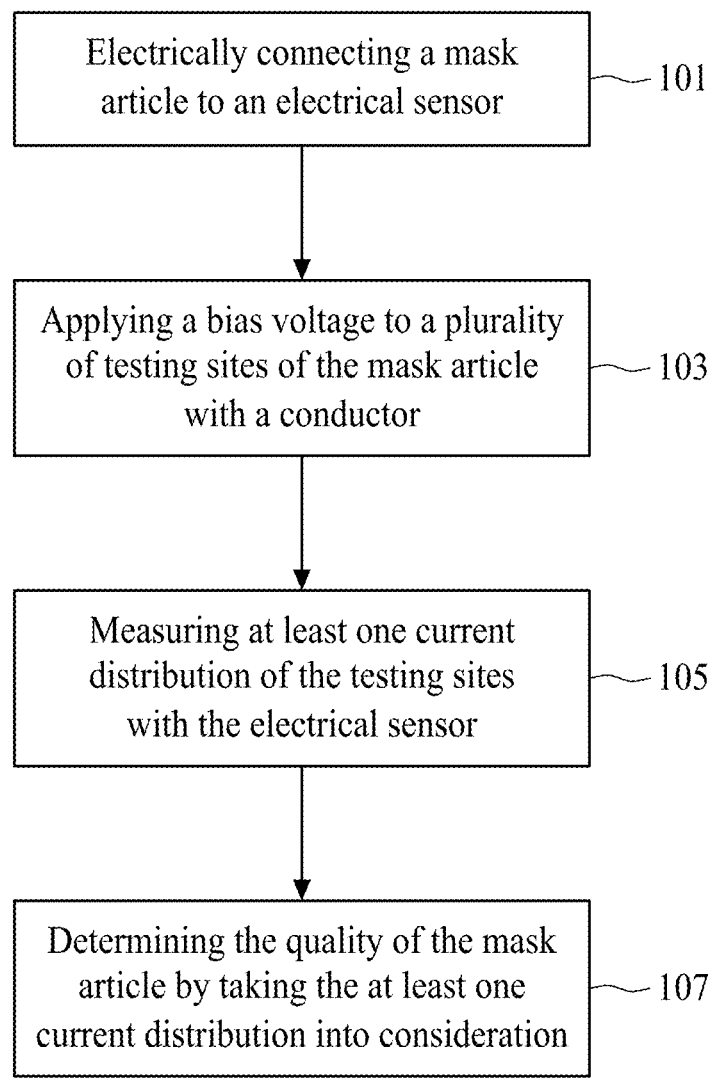
FIG. 1 illustrates a flow chart listing the steps for testing a mask article according to one embodiment of the present disclosure.

FIG. 1 illustrates a flow chart listing the steps for testing a mask article according to one embodiment of the present disclosure. In one embodiment of the present disclosure, the testing method comprises a step 101 of electrically connecting the mask article to an electrical sensor, a step 103 of applying a bias voltage to a plurality of testing sites of the mask article with a conductor, a step 105 of measuring at least one current distribution of the testing sites with the electrical sensor, and a step 107 of determining the quality of the mask article by taking the at least one current distribution into consideration.

Figure 2:
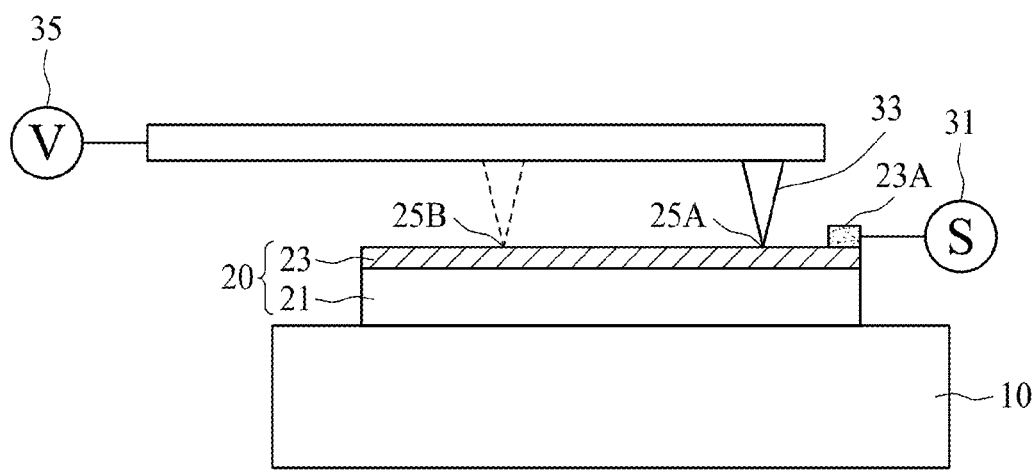
FIG. 2 and FIG. 3 are schematic diagrams illustrating the testing of a mask article according to one embodiment of the present disclosure.
Figure 3:
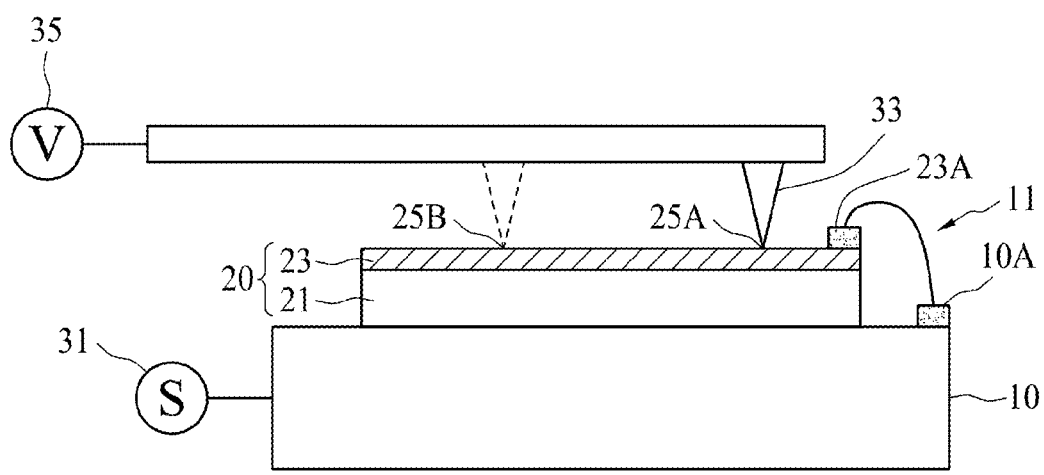

FIG. 2 and FIG. 3 are schematic diagrams illustrating the testing of a mask article 20 according to one embodiment of the present disclosure. In an exemplary embodiment of the present disclosure, the mask article 20 comprises a substrate 21 a conductive layer 23 such as a MoSi layer. In one embodiment of the present disclosure, the substrate 21 is a quartz substrate or a Ti-doped silicon oxide glass substrate. In one embodiment of the present disclosure, the step 101 of electrically connecting of the mask article 20 to an electrical sensor 31 can be accomplished by forming at least one contact 23A on the conductive layer 23 of the mask article 20, and contacting a sensing probe (not shown in the drawings) of the electrical sensor 31 with the at least one contact 23A of the conductive layer 23, as shown in FIG. 2. In another exemplary embodiment of the present disclosure, the electrical connecting of the mask article 20 to an electrical sensor 31 can be accomplished by placing the mask article 20 on a stage 10 electrically connected to the electrical sensor 31 and forming an electrical connection between the mask article 20 and the stage 10, as shown in FIG. 3. In a preferred embodiment of the present disclosure, the electrical connection between the mask article 20 and the stage 10 includes the contact 23A of the conductive layer 23, a contact 10A on the stage 10 and a wire 11 connecting the contact 23A and the contact 10A.

Referring to FIG. 2 or FIG. 3, in one embodiment of the present disclosure, the step 103 of applying a bias voltage to a plurality of testing sites of the mask article 20 with a conductor 33 can be accomplished by electrically connecting the conductor 33 to a bias voltage 35 such as a voltage source and contacting the plurality of testing sites of the mask article 20 with the conductor 33. In one exemplary embodiment of the present disclosure, the conductor 33 is an electrically conductive tip. In one exemplary embodiment of the present disclosure, the step 105 of measuring at least one current distribution of the testing sites with the electrical sensor 31 can be accomplished by measuring the current from the bias voltage 35, through the conductor 33 and the mask article 20 to the electrical sensor 31. In a preferred embodiment of the present disclosure, the steps 103 and 105 can be implemented by contacting a first site 25A of the mask article 20 with the conductor 33, measuring a first current value passing through the first site 25A of the mask article 20 with the electrical sensor 31, moving the conductor 33 to contact a second site 25B of the mask article 20, measuring a second current value passing through the second site of the mask article 20 with the electrical sensor 33 and so on.

Figure 4A:
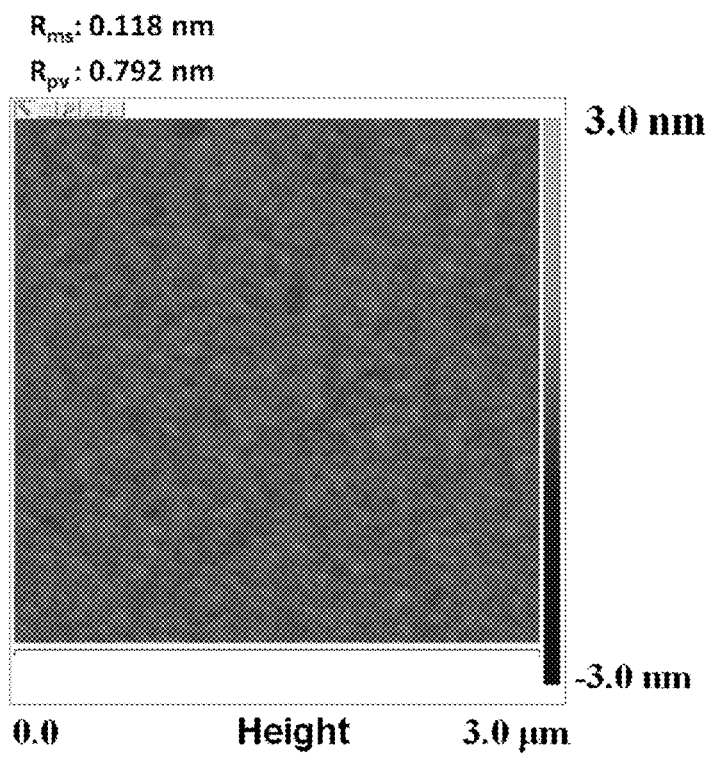
FIG. 4A, FIG. 5A and FIG. 6A are topographic images for three mask blanks (designated as P-0.5, P-3 and P-5)
Figure 4B:
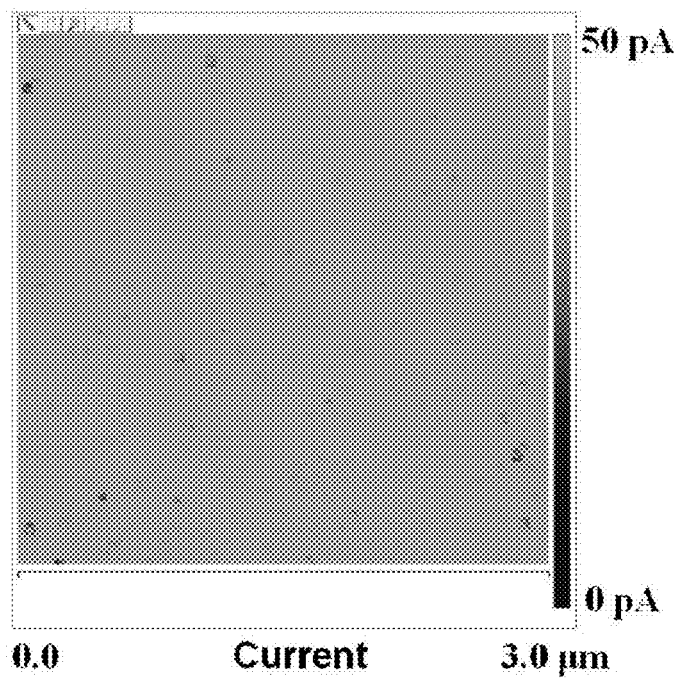
FIG. 4B, FIG. 5B and FIG. 6B shows the current distribution images for three mask blanks (designated as P-0.5, P-3 and P-5)
Figure 5A:
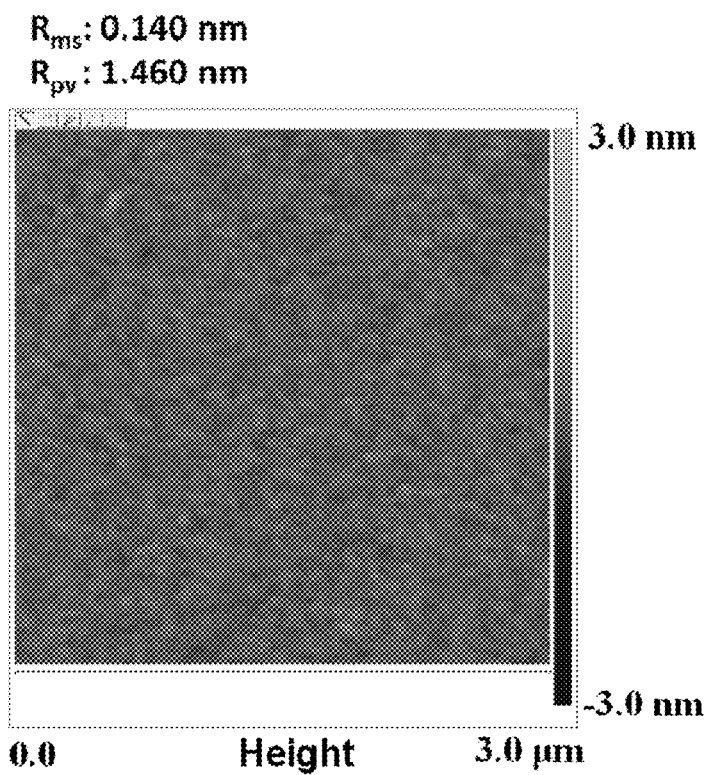
Figure 5B:
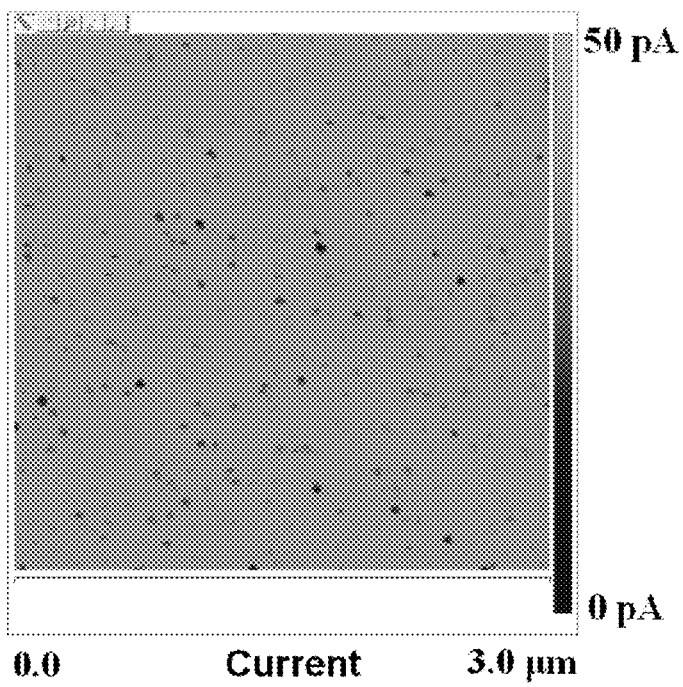
Figure 6A:
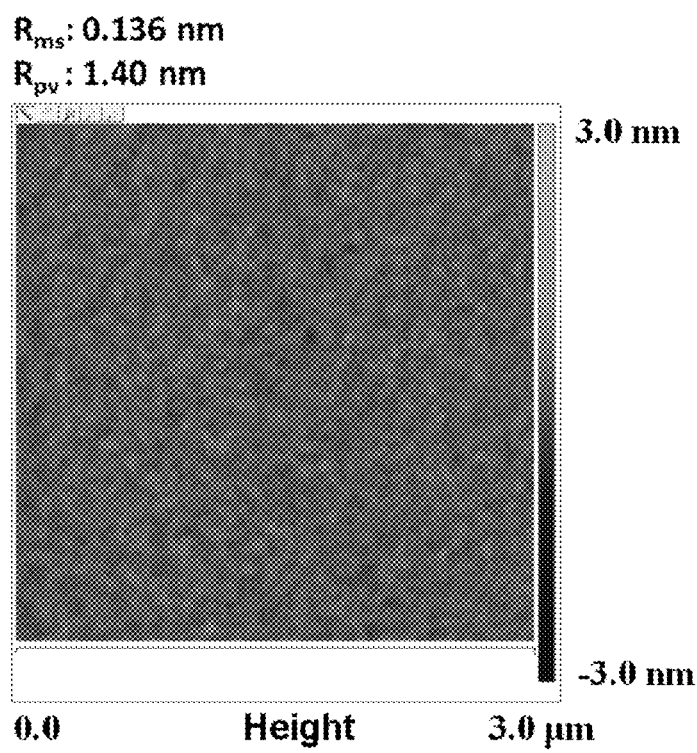
Figure 6B:
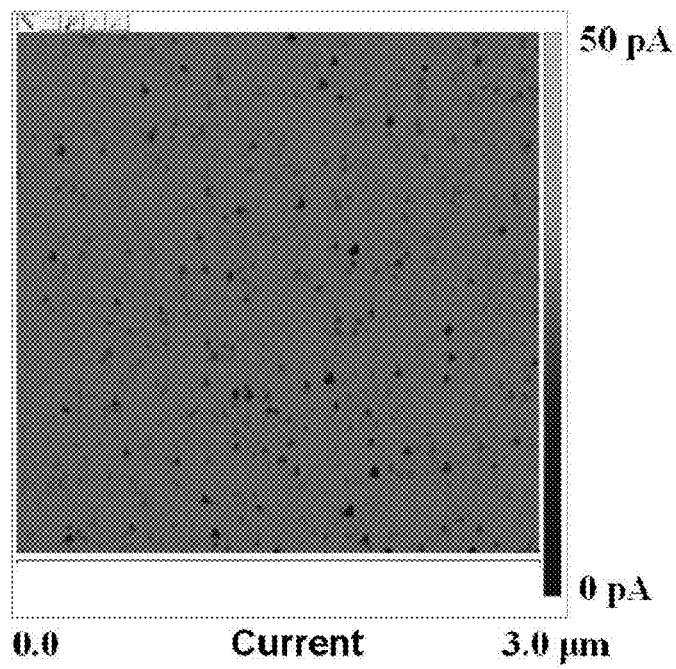
Figure 7A:
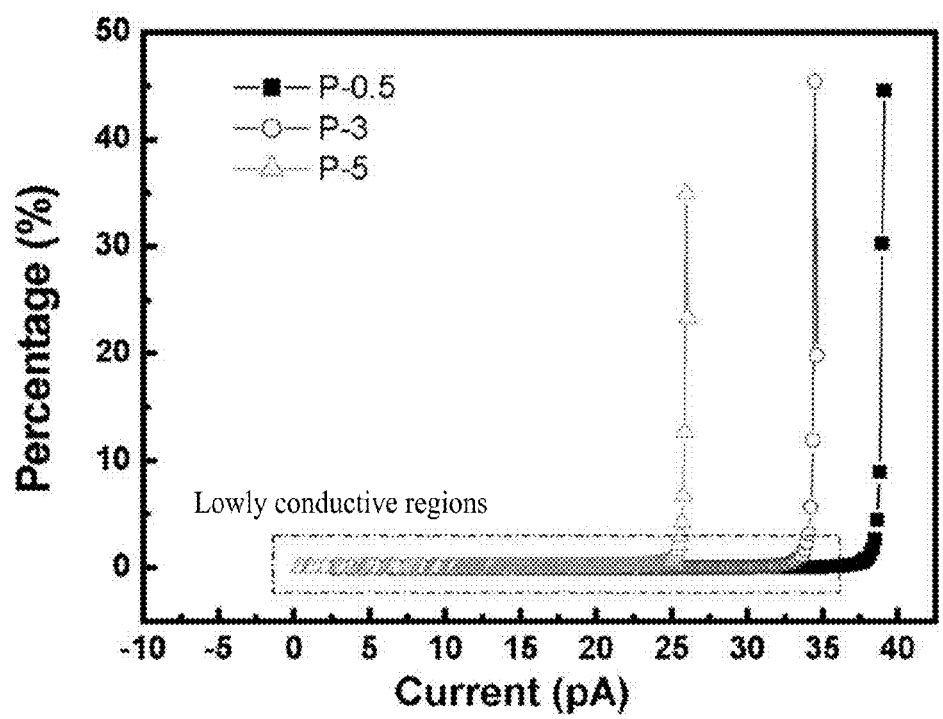
FIG. 7A is a histogram of the current distribution images (65536 data points in the current distribution image of 3×3 $\mu m^2$) in FIG. 4B, FIG. 5B and FIG. 6B for the mask blanks (P-0.5, P-3 and P-5)
Figure 7B:
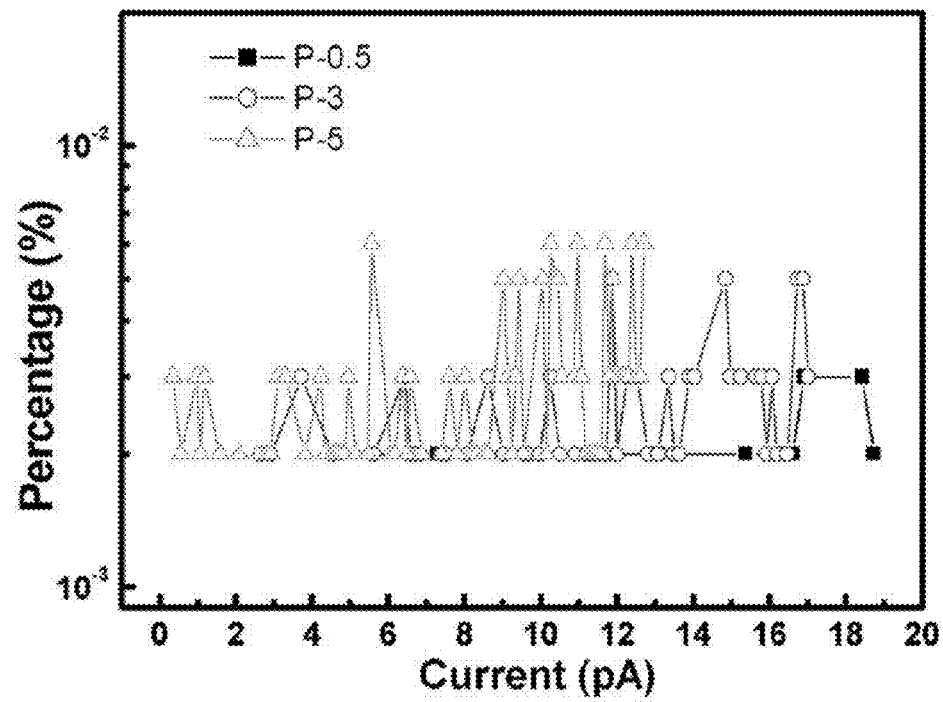
FIG. 7B shows the current distributions for lowly conductive regions in FIG. 7A.

FIG. 4A, FIG. 5A and FIG. 6A are topographic images, and FIG. 4B, FIG. 5B and FIG. 6B are current distribution images for three mask blanks (designated as P-0.5, P-3 and P-5) with a conductive layer (MoSi layer) on a quartz substrate, wherein the scanning area is 3×3 μm$^2$ with 256×256 testing sites. The three mask blanks experience different cleaning processes at a megasonic power of 0.5 W, 3W and 5W, and the current distribution images are acquired with a bias voltage of 0.1V applied to the conductor 33 of a conductive AFM (atomic force microscopy) during scanning FIG. 7A is a histogram of the current distribution images in FIG. 4B, FIG. 5B and FIG. 6B. FIG. 7B shows the current distributions for lowly conductive regions in FIG. 7A.

For the topographic images, the Rms values are 0.118 nm, 0.140 nm and 0.136 nm, and Rpv values are 0.792 nm, 1.460 nm and 1.40 nm, respectively, which indicates that their surface roughness is similar. For the current distribution images, the characteristic parameters include the average currents, standard deviations, and relative standard deviations of average current, which are listed in Table 1. The standard deviation is a root mean square of the current $(I_{rms}=(\Sigma(Ii-Iav)^2/n)^{1/2}$. The Relative standard deviation is equal to $I_{rms}/I_{av}$; a smaller value indicates more uniform distribution of current.

TABLE 1

| | Average current $I_{av}$ (pA) | Standard deviation $I_{rms}$ (pA) | Relative standard deviation (%) |
|---|---|---|---|
| P-0.5 | 38.8 | 0.9 | 2.3 |
| P-3 | 34.2 | 1.40 | 4.1 |
| P-5 | 25.6 | 1.49 | 5.8 |

Figure 8A:
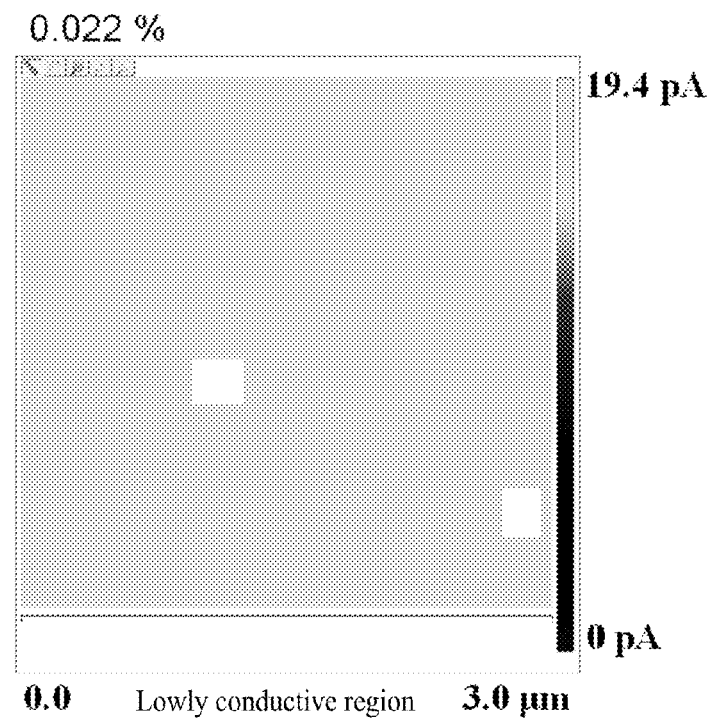
FIG. 8A, FIG. 9A, and FIG. 10A are current distribution images for lowly conductive regions of the mask blanks (P-0.5, P-3 and P-5)
Figure 8B:
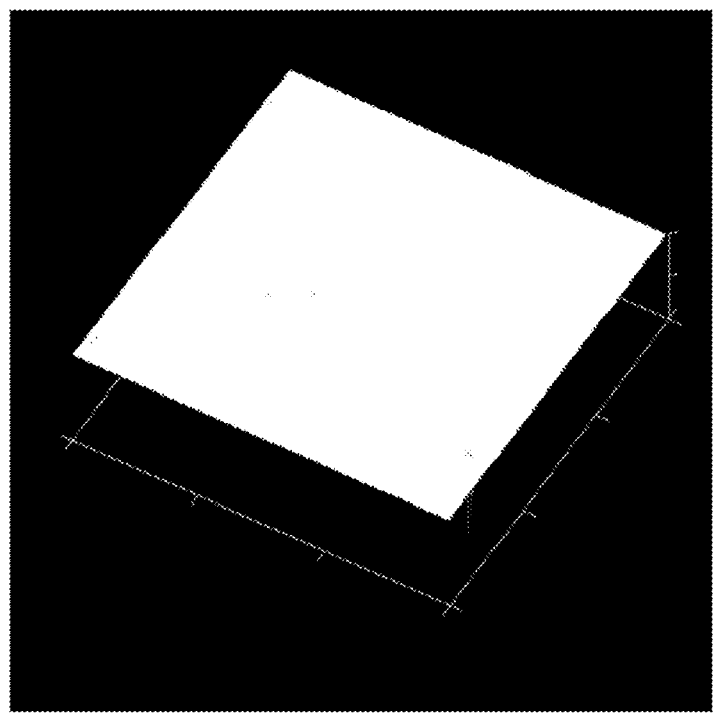
FIG. 8B, FIG. 9B, and FIG. 10B are 3-D profiles for the mask blanks (P-0.5, P-3 and P-5)
Figure 9A:
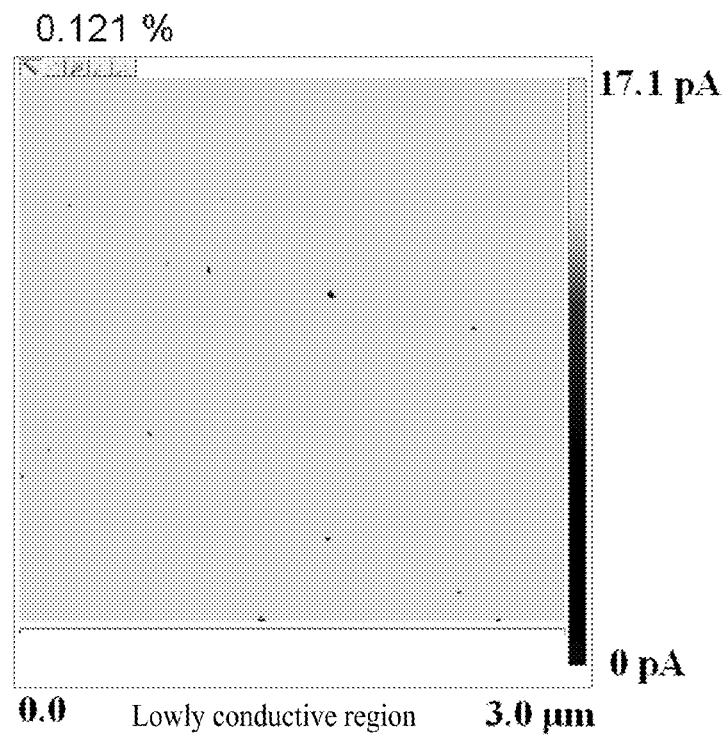
Figure 9B:
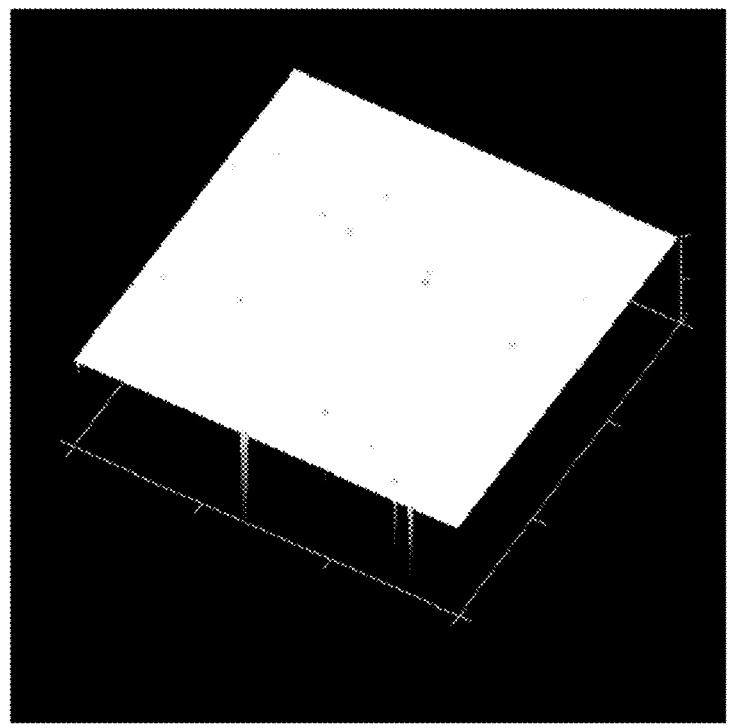
Figure 10A:
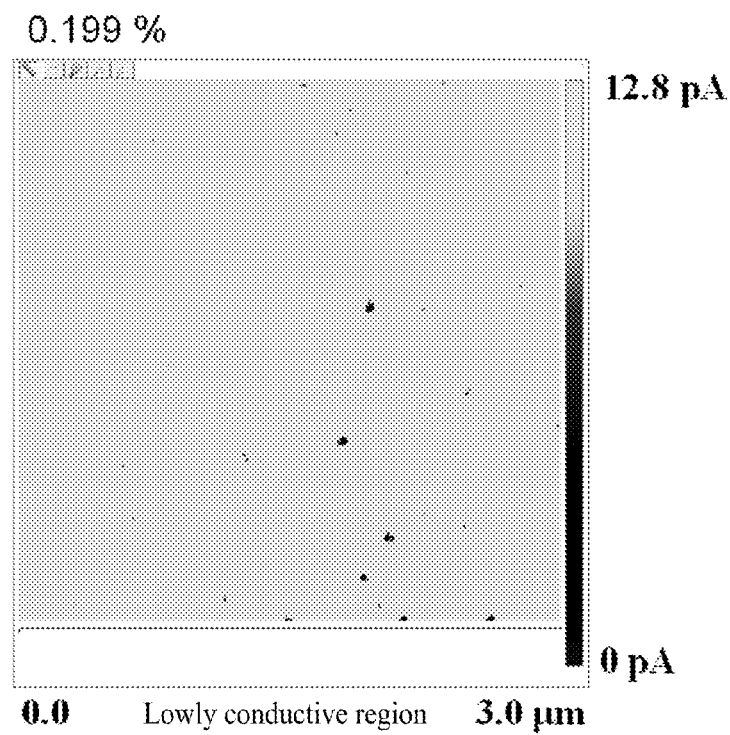
Figure 10B:
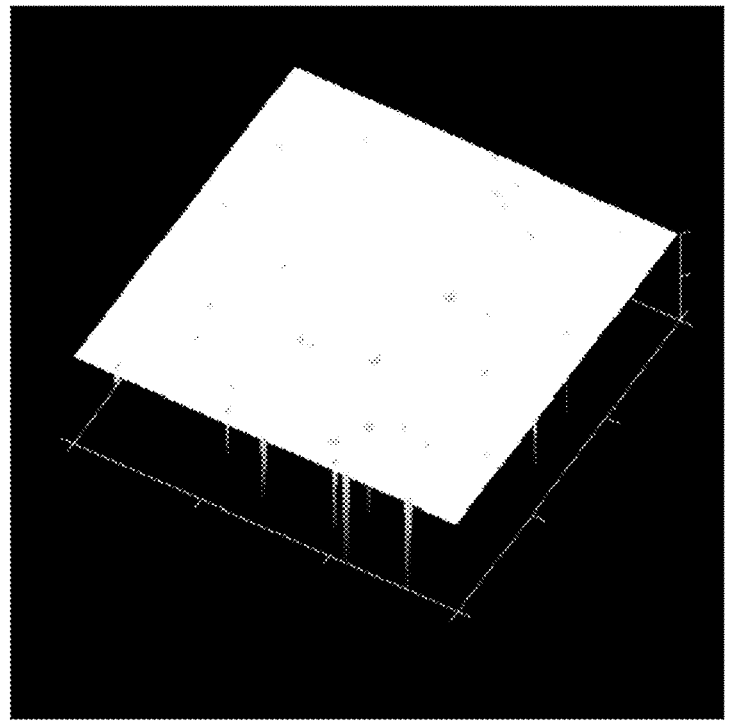

FIG. 8A, FIG. 9A, and FIG. 10A are current distribution images for lowly conductive regions for the mask blanks (P-0.5, P-3 and P-5), and FIG. 8B, FIG. 9B, and FIG. 10B are 3-D profiles for the mask blanks (P-0.5, P-3 and P-5), to respectively. If the area has a local current two times lower than the average current, then it is defined as a "lowly conductive region". The percentage of coverage of the lowly conductive regions on the P-0.5, P-1 and P-5 mask blanks are 0.022%, 0.121% and 0.199%, respectively. The lowly conductive regions could result from the regions of defects in the MoSi layer, through which less is current passes to generate a local lower current. In addition, the lowly conductive regions for all the three mask blanks distribute randomly around the surface of the three mask blanks. Furthermore, the lowly conductive regions, with sizes ranging from 12 to 95 nm, can be considered defects, and thus become the origin of lowly conductive regions for CAFM measurement on the MoSi layer. In one embodiment of the present disclosure, the step 107 of determining the quality of the mask article can be accomplished by taking the at least one current distribution into consideration; for example, comparing current values of the plurality of testing sites with the average current, and counting a number of the testing sites with a current value lower than a threshold value such as the average current.

Figure 11:
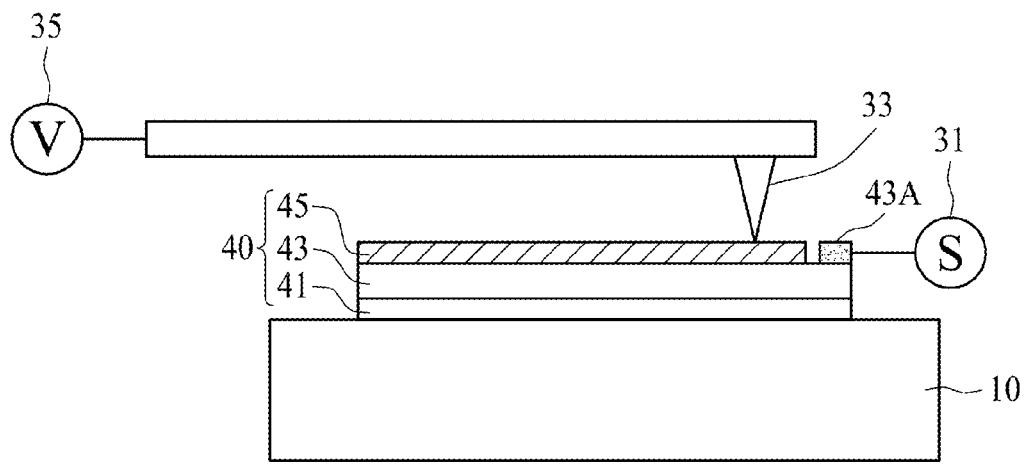
FIG. 11 is a schematic diagram illustrating the testing of a mask article according to one embodiment of the present disclosure.

FIG. 11 is a schematic diagram illustrating the testing of a mask article 40 according to one embodiment of the present disclosure. In an exemplary embodiment of the present disclosure, the mask article 40 comprises a substrate 41, a conductive layer 43 such as a chromium layer, and a dielectric layer 45 such as a chromium oxide layer. In one embodiment of the present disclosure, the step 101 of electrically connecting of the mask article 40 to an electrical sensor 31 can be accomplished by forming at least one contact 43A on the conductive layer 43 of the mask article 40, and contacting a sensing probe of the electrical sensor 31 with the at least one contact 43A of the conductive layer 43. In one embodiment of the present disclosure, the substrate 41 is a quartz substrate or a Ti-doped silicon oxide glass substrate. In another exemplary embodiment of the present disclosure, the electrically connecting of the mask article 40 to the electrical sensor 31 can be accomplished by the electrical connection similar to that shown in FIG. 3.

Figure 12A:
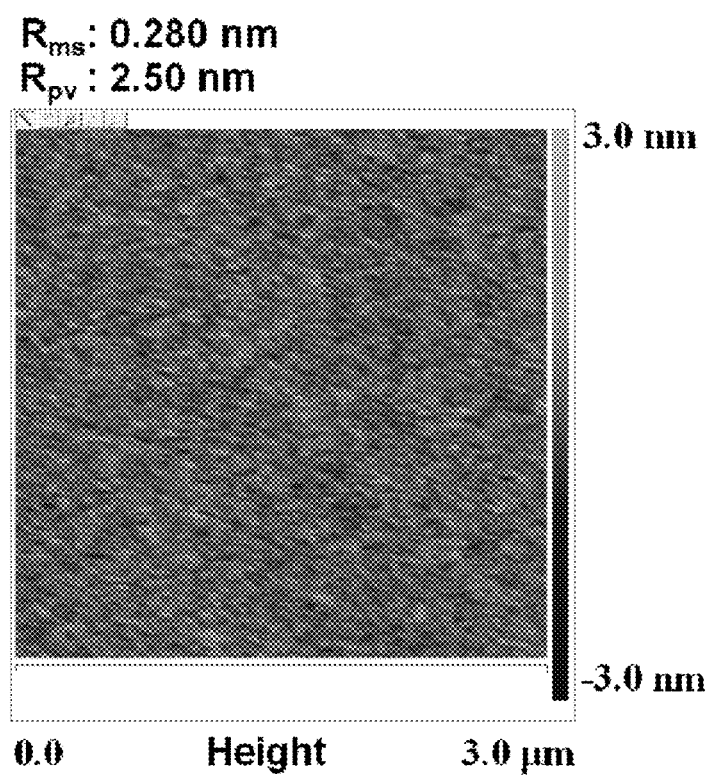
FIG. 12A, FIG. 13A and FIG. 14A are topographic images for three mask blanks (designated as M-0.5, M-1 and M-2)
Figure 12B:
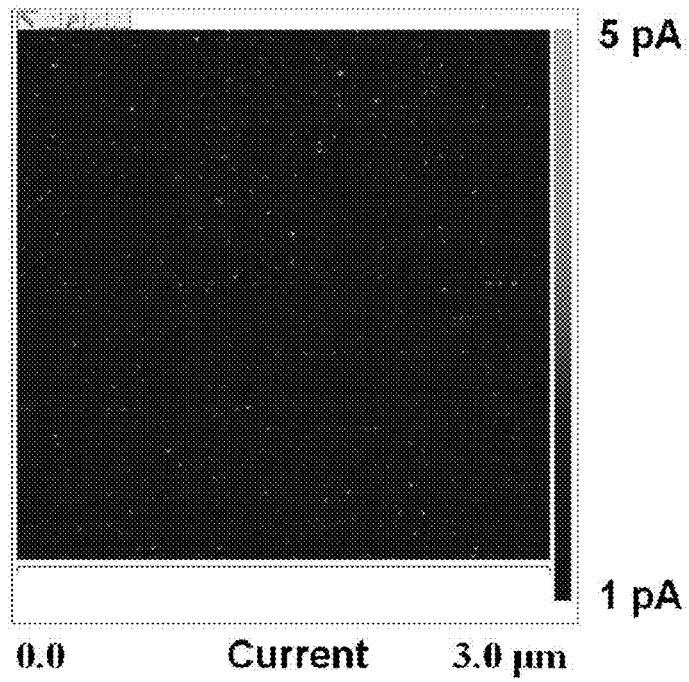
FIG. 12B, FIG. 13B and FIG. 14B are current distribution images for three mask blanks (designated as M-0.5, M-1 and M-2)
Figure 13A:
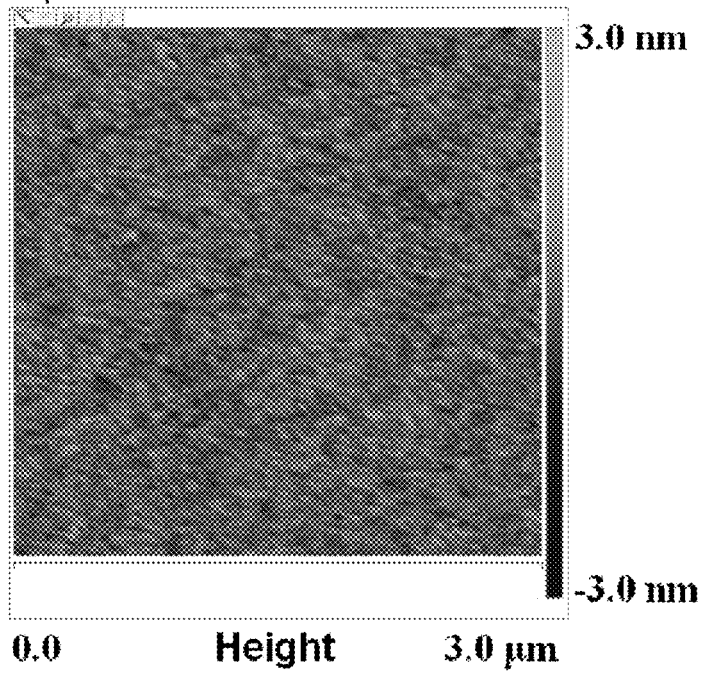
Figure 13B:
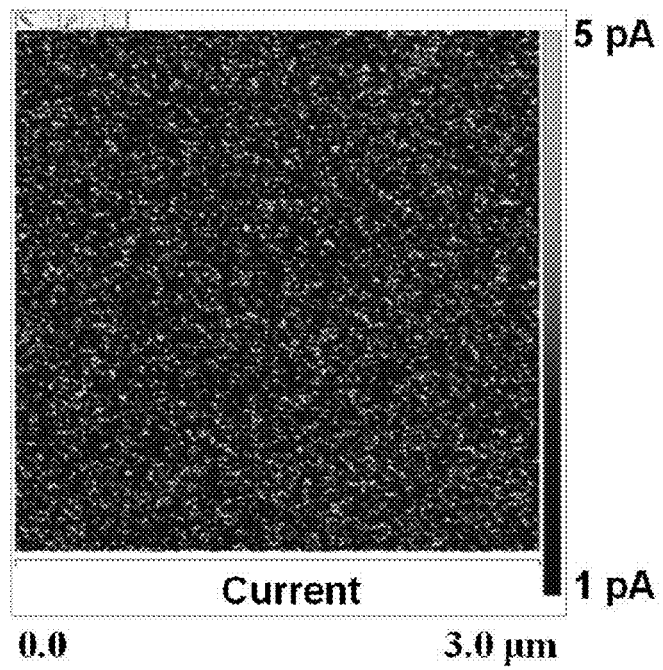
Figure 14A:
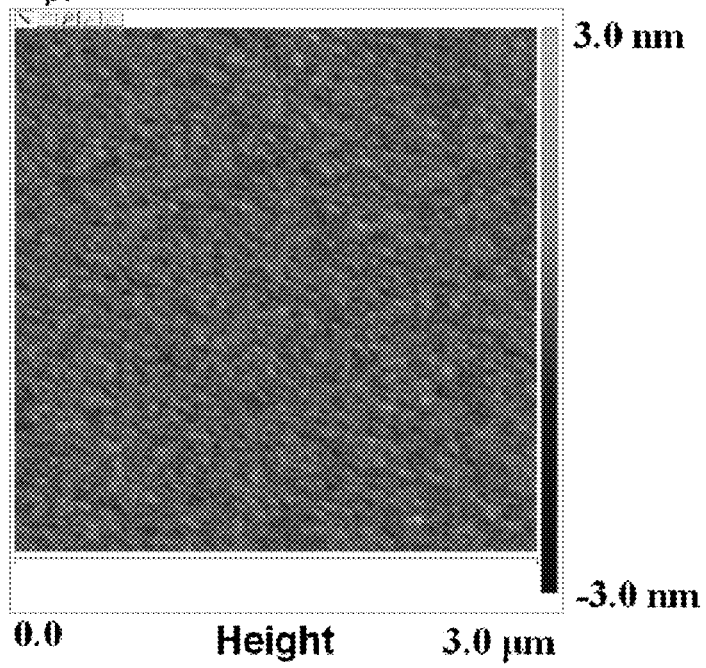
Figure 14B:
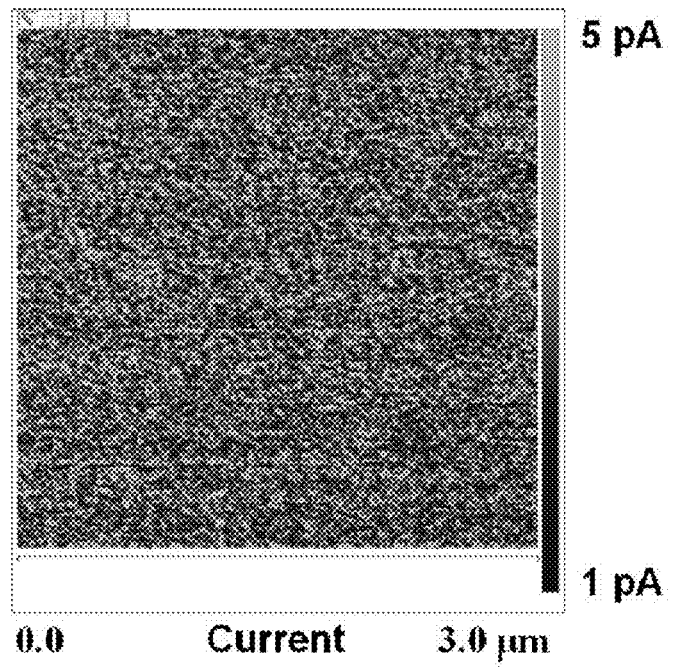
Figure 15A:
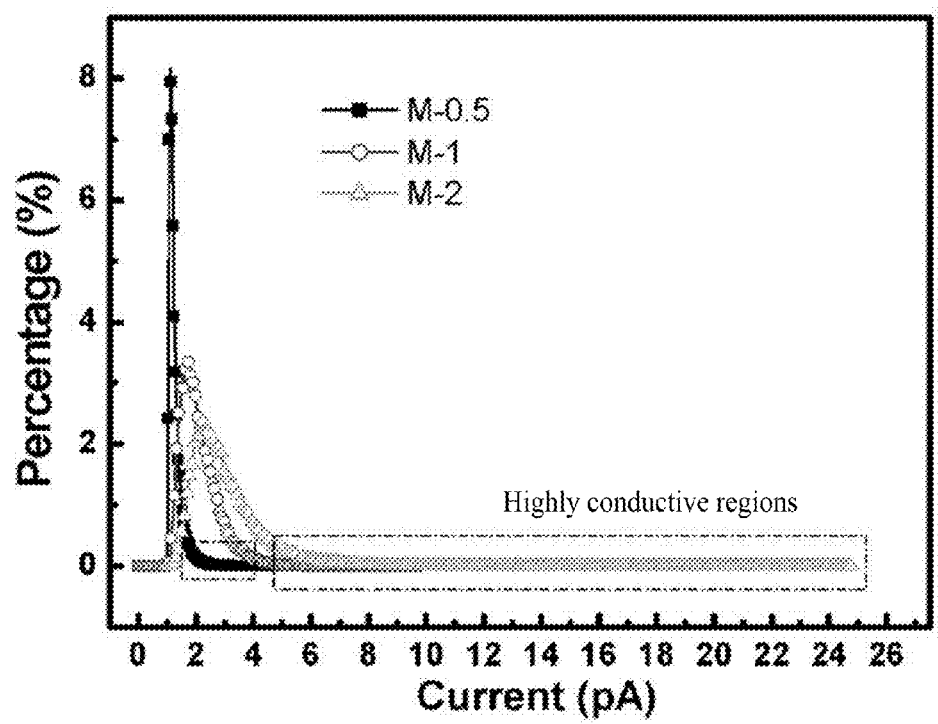
FIG. 15A is a histogram of the current distribution images in FIG. 12B, FIG. 13B and FIG. 14B for the mask blanks (P-0.5, P-3 and P-5)
Figure 15B:
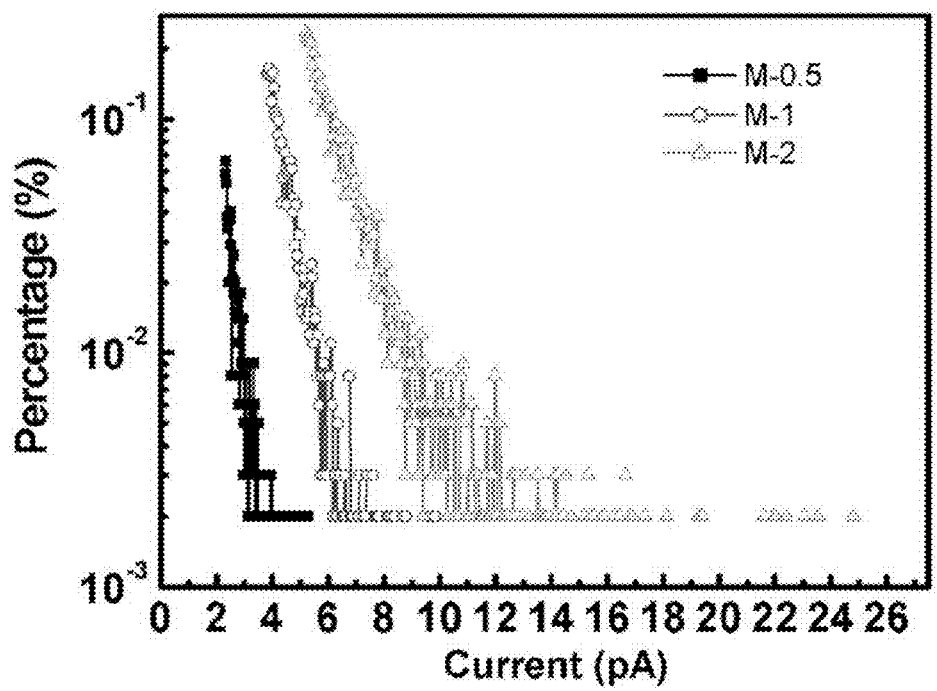
FIG. 15B shows the current distributions for highly conductive regions in FIG. 15A.

FIG. 12A, FIG. 13A and FIG. 14A are topographic images, and FIG. 12B, FIG. 13B and FIG. 14B are current distribution images for three mask blanks (designated as M-0.5, M-1 and M-2) with a chromium oxide layer and a chromium layer on a quartz substrate, wherein the scanning area is 3×3 µm² with 256×256 testing sites. The three mask blanks experience different cleaning processes at a megasonic power of 0.5 W, 1 W and 2 W, and the current distribution images are acquired with a bias voltage of 0.1V applied to the conductor 33 of a conductive AFM (atomic force microscopy) during scanning FIG. 15A is a histogram of the current distribution images in FIG. 12B, FIG. 13B and FIG. 14B, and FIG. 15B shows the current distributions for highly conductive regions in FIG. 15A.

For the topographic images, the $R_{ms}$, values are 0.280 nm, 0.285 nm and 0.219 nm, and $R_{pv}$ values are 2.50 nm, 2.55 nm and 2.23 nm, respectively, which indicates that their surface roughness are similar. For the current distribution images, the characteristic parameters include the average currents, standard deviations, and relative standard deviations of average current which are listed in Table 2. The standard deviation is a root mean square of the current $(I_{rms}=(\Sigma(Ii-Iav)^2/n)^{1/2}$. The Relative standard deviation is equal to $I_{rms}/I_{av}$; a smaller value indicates more uniform distribution of current.

TABLE 2

| | Average current $I_{av}$ (pA) | Standard deviation $I_{rms}$ (pA) | Relative standard deviation (%) |
|---|---|---|---|
| M-0.5 | 1.16 | 0.1 | 8.6 |
| M-1 | 1.89 | 0.49 | 25.9 |
| M-2 | 2.59 | 0.81 | 31.3 |

Figure 16A:
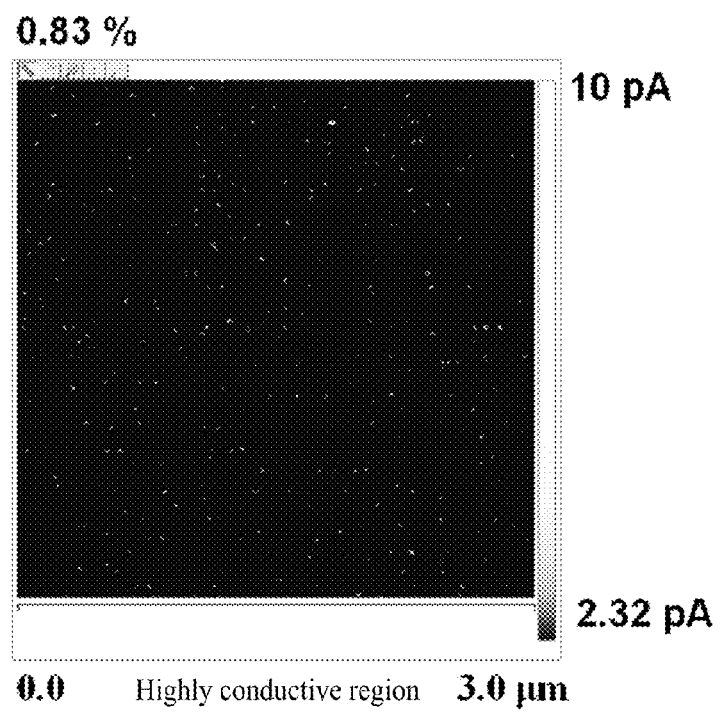
FIG. 16A, FIG. 17A and FIG. 18A are current distribution images for highly conductive regions for the mask blanks (M-0.5, M-1 and M-2)
Figure 16B:
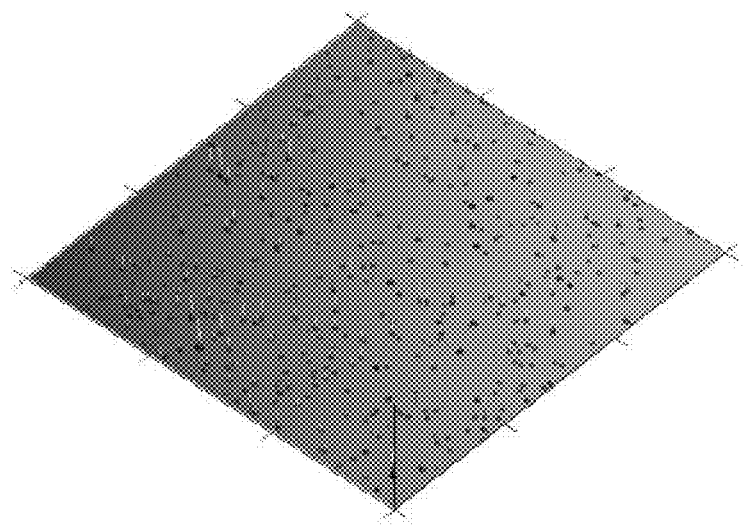
FIG. 16B, FIG. 17B and FIG. 18B are 3-D profiles for the mask blanks (M-0.5, M-1 and M-2)
Figure 17A:
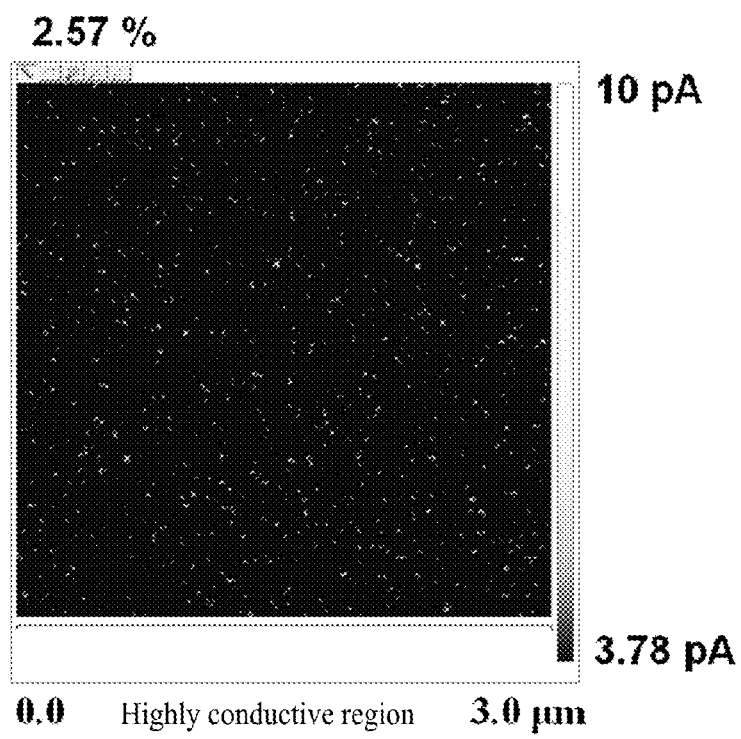
Figure 17B:
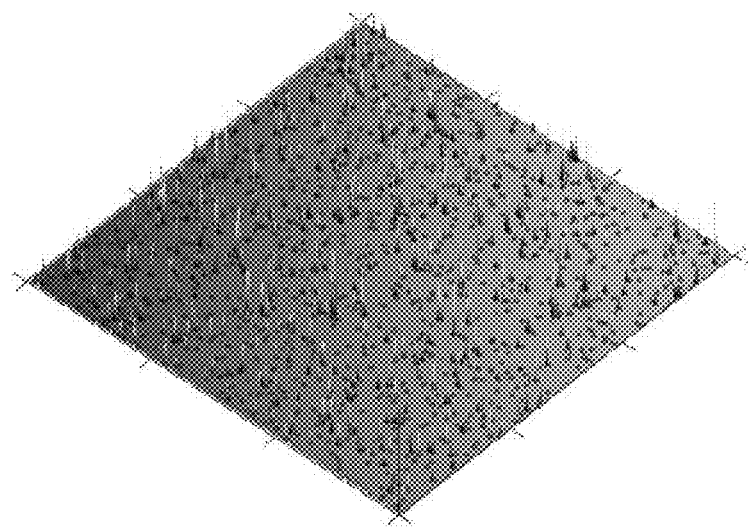
Figure 18A:
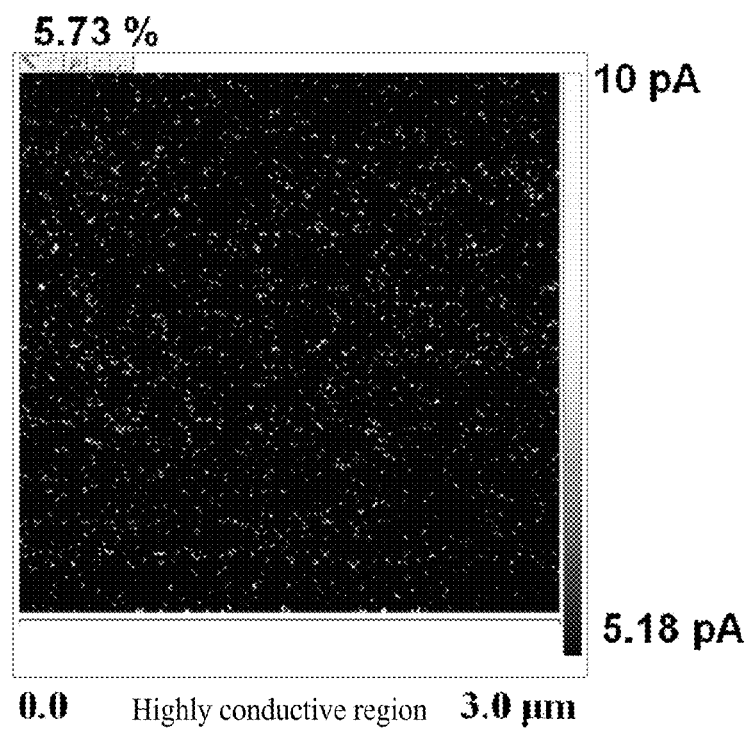
Figure 18B:
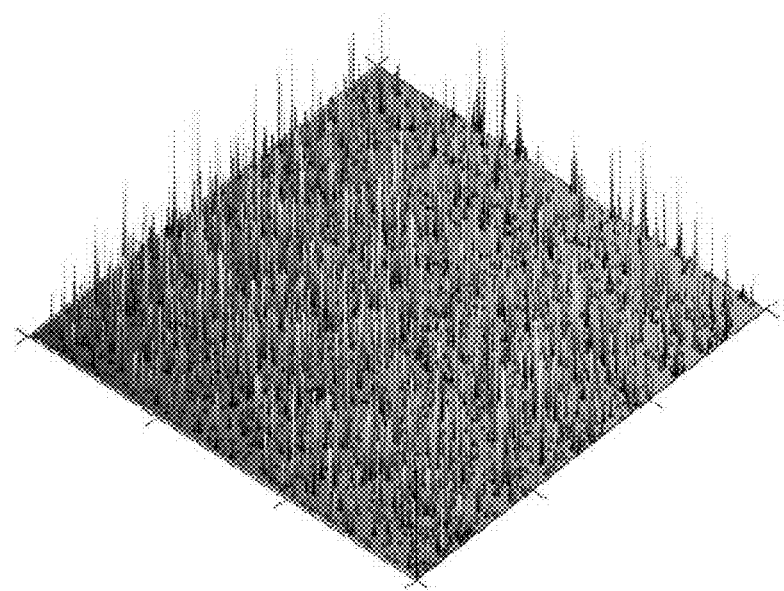

FIG. 16A, FIG. 17A and FIG. 18A are current distribution images for highly conductive regions, and FIG. 16B, FIG. 17B and FIG. 18B are 3-D profiles for the mask blanks (M-0.5, M-1 and M-2), respectively. If the area has a local current two times larger than the average current, then it is defined as a "highly conductive region". The percentage of coverage of the highly conductive regions on the M-0.5, M-1 and M-2 mask blanks are 0.83%, 2.57% and 5.73%, respectively. The electrical conductivity of chromium oxide layer ($\sim 10^4$ S/m at room temperature) is lower than that of the chromium layer ($7.9 \times 10^6$ S/m at room temperature). The highly conductive regions could result from the regions of damages in the chromium oxide layer, through which current preferentially passes to generate a local higher current. In addition, the highly conductive regions for all three mask blanks distribute randomly around their surfaces. Furthermore, the highly conductive regions, with sizes ranging from 15 to 100 nm, can be considered defects, and thus become the origin of highly conductive regions for CAFM measurement. In one embodiment of the present disclosure, the step 107 of determining the quality of the mask article can be accomplished by taking the at least one current distribution into consideration; for example, comparing current values of the testing sites with the average current, and counting a number of the testing sites with a current value higher than a threshold is value such as the average current.

Figure 19:
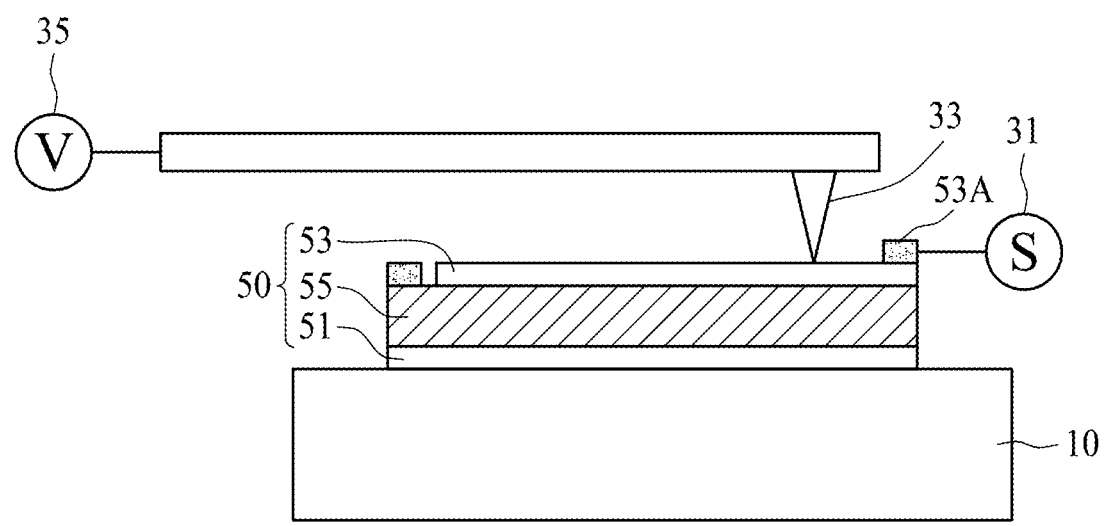
FIG. 19 and FIG. 20 are schematic diagrams illustrating the testing of a mask article with a multi-layer structure according to one embodiment of the present disclosure.
Figure 20:
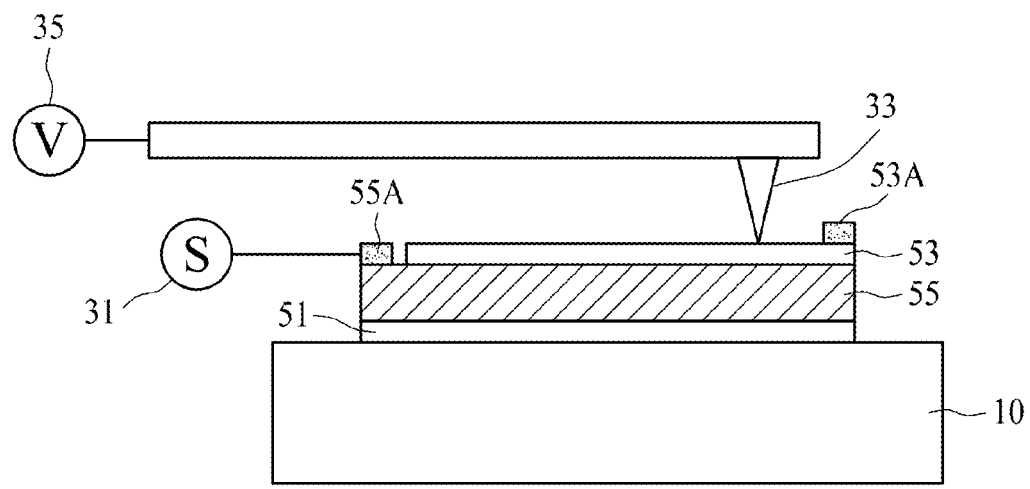

FIG. 19 and FIG. 20 are schematic diagrams illustrating the testing of a mask article 50 with a multi-layer structure according to one embodiment of the present disclosure. In an exemplary embodiment of the present disclosure, the mask article 50 is a mask blank comprising a substrate 51, a first layer 53 with at least one first contact 53A, and a second layer 55 with at least one second contact 55A. In one embodiment of the present disclosure, the substrate 51 is a quartz substrate or a Ti-doped silicon oxide glass substrate. In a preferred embodiment of the present disclosure, as shown in FIG. 19, the testing method of the mask article 50 comprises the steps of electrically connecting the first contact 53A to the electrical sensor 31, applying the bias voltage 35 through the plurality of testing sites to the first layer 53 with the conductor 33, and measuring a first current distribution of the first layer 53 with the electrical sensor 31; subsequently, as shown in FIG. 20, the testing method of the mask article 50 performs the steps of electrically connecting the second contact 55A to the electrical sensor 31, applying the bias voltage 35 through the plurality of testing sites to the first layer 53 with the conductor 33 and measuring a second current distribution of the second layer 55 with the electrical sensor 31. In another exemplary embodiment of the present disclosure, the electrical connecting of the mask article 50 to the electrical sensor 31 can be accomplished by the electrical connection similar to that shown in FIG. 3.

In one exemplary embodiment of the present disclosure, the testing method of the mask article 50 determines the quality of the mask article 50 by taking the first current distribution and the second current distribution into consideration. For example, the second current distribution represents the electrical effect substantially both of the first layer 53 and the second layer 55, while the first current distribution represents the electrical effect substantially of the first layer 53 only. Subtracting the first current distribution from the second current distribution substantially results in the electrical property of the second layer 55.

Figure 21:
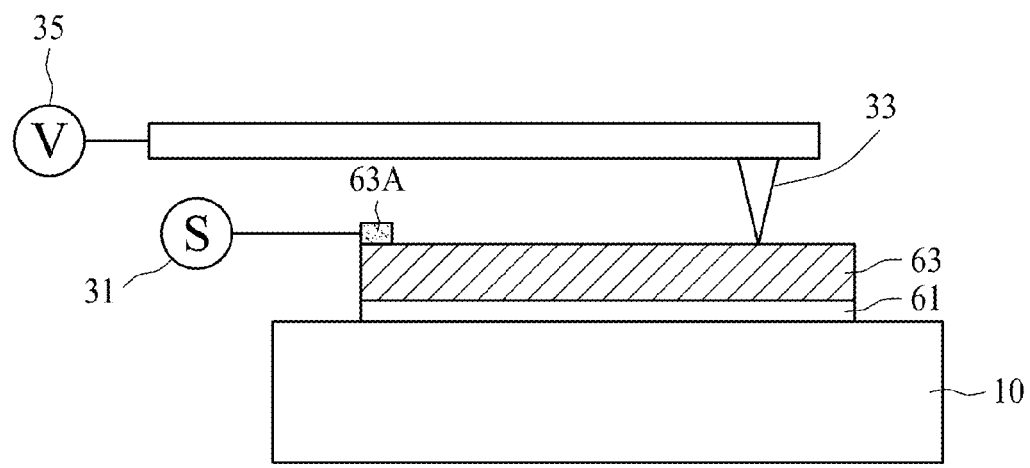
FIG. 21 and FIG. 22 are schematic diagrams illustrating the testing of a mask article with a multi-layer structure according to another embodiment of the present disclosure.
Figure 22:
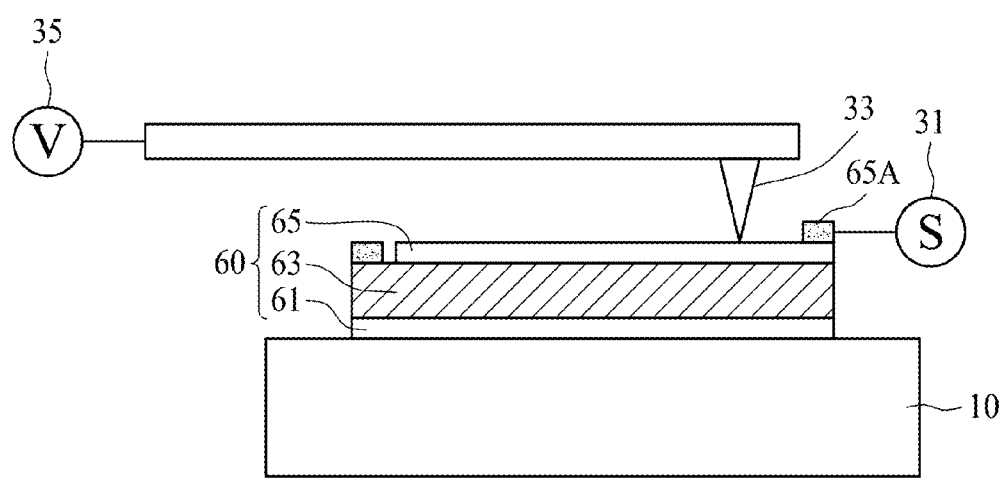

FIG. 21 and FIG. 22 are schematic diagrams illustrating the testing of a mask article 60 with a multi-layer structure according to one embodiment of the present disclosure. In an exemplary embodiment of the present disclosure, as shown in FIG. 21, the testing method of the mask article 60 comprises the steps of forming a first layer 63 with at least one first contact 63A on a substrate 61, electrically connecting the first contact 63A to the electrical sensor 31, applying the bias voltage 35 through the plurality of testing sites to the first layer 63 with the conductor 33 and measuring a first current distribution of the first layer 63 with the electrical sensor 31. Subsequently, as shown in FIG. 22, the testing method of the mask article 60 performs the steps of forming a second layer 65 with at least one second contact 65A, electrically connecting the second contact 65A to the electrical sensor 31, applying the bias voltage 35 through the plurality of testing sites to the second layer 65 with the conductor 33 and measuring a second current distribution of the second layer 65 with the electrical sensor 31. In one embodiment of the present disclosure, the substrate 61 is a quartz substrate or a Ti-doped silicon oxide glass substrate. In one embodiment of the present disclosure, the testing method of the mask article 60 determines the quality of the mask article 60 by taking the first current distribution and the second current distribution into consideration. In another exemplary embodiment of the present disclosure, the electrical connecting of the mask article 60 to the electrical sensor 31 can be accomplished by the electrical connection similar to that shown in FIG. 3.

Figure 23:
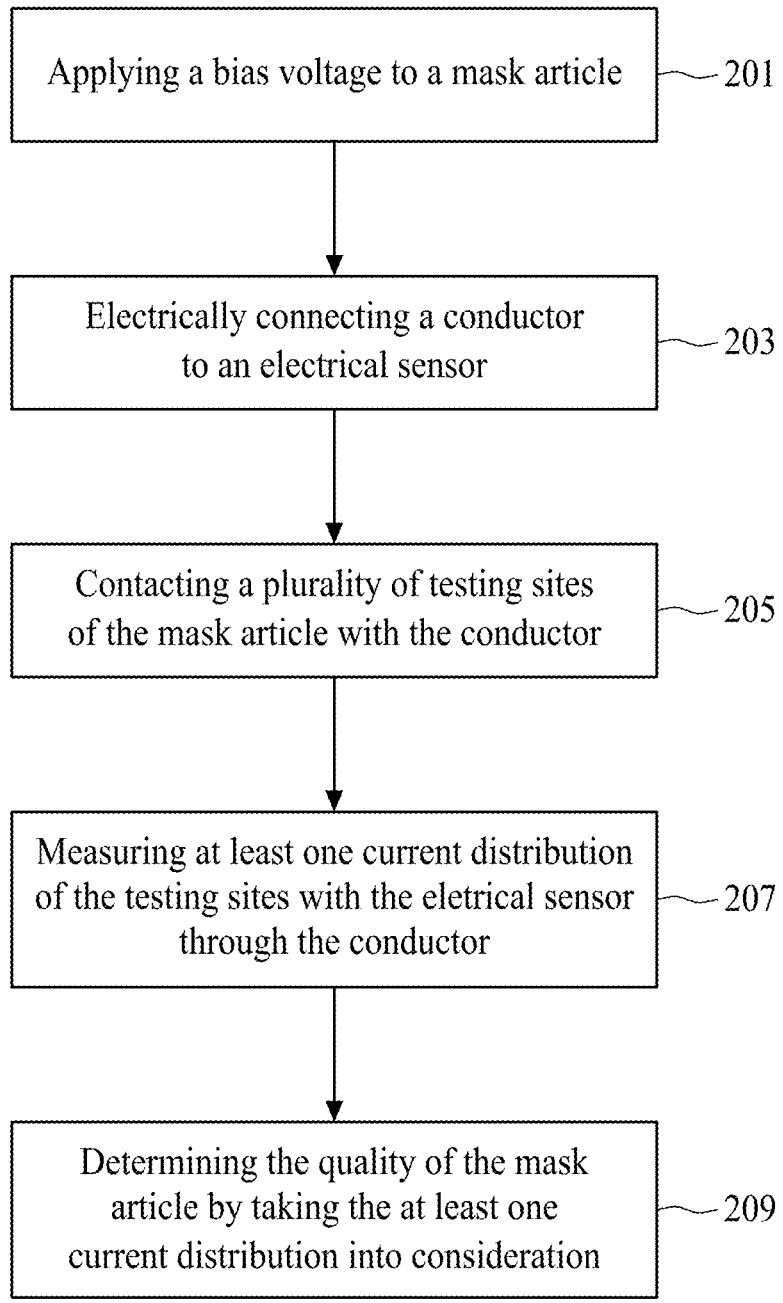
FIG. 23 illustrates a flow chart listing the steps for testing a mask article according to another embodiment of the present disclosure.

FIG. 23 illustrates a flow chart listing the steps for testing a mask article according to another embodiment of the present disclosure. In one embodiment of the present disclosure, the testing method comprises a step 201 of applying a bias voltage 35 to the mask article, a step 203 of electrically connecting a conductor to an electrical sensor, a step 205 of contacting a plurality of testing sites of the mask article with the conductor, a step 207 of measuring at least one current distribution of the testing sites with the electrical sensor through the conductor, and a step 209 of determining the quality of the mask article by taking the current distribution into consideration.

Figure 24:
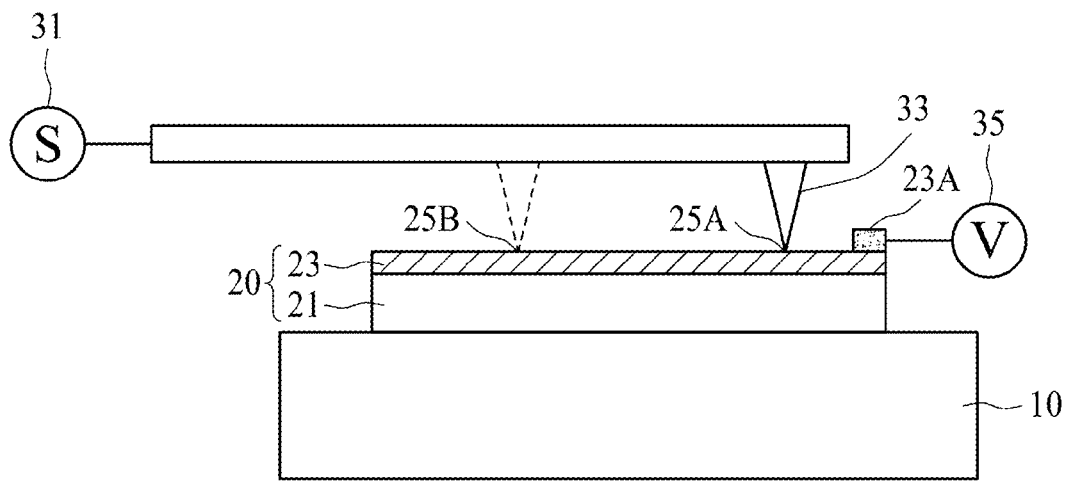
FIG. 24 and FIG. 25 are schematic diagrams illustrating the testing of a mask article according to another embodiment of the present disclosure.
Figure 25:
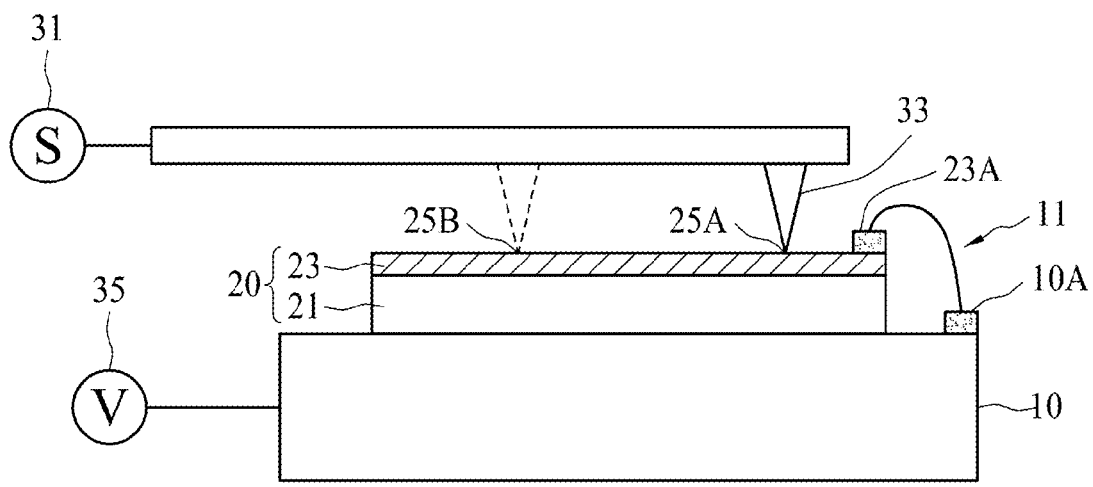

FIG. 24 and FIG. 25 are schematic diagrams illustrating the testing of a mask article 20 according to another embodiment of the present disclosure. In an exemplary embodiment of the present disclosure, the mask article 20 comprises a substrate 21 such as a quartz substrate and a conductive layer 23 such as a MoSi layer. In one embodiment of the present disclosure, the step 201 of applying a bias voltage 35 to the mask article 20 can be accomplished by forming at least one contact 23A on the conductive layer 23 of the mask article 20, and contacting a power probe of bias voltage 35 such as a voltage source with at least one contact 23A of the conductive layer 23, as shown in FIG. 24.

In another exemplary embodiment of the present disclosure, the step 201 of applying a bias voltage 35 to the mask article 20 can be accomplished by placing the mask article 20 on a stage 10 electrically connected to the bias voltage 35, and forming an electrical connection between the mask article 20 and the stage 10, as shown in FIG. 25. In a preferred embodiment of the present disclosure, the electrical connection between the mask article 20 and the stage 10 includes the contact 23A of the conductive layer 23, a contact 10A on the stage 10, and a wire 11 connecting the contact 23A and the contact 10A.

In one embodiment of the present disclosure, the conductor 33 is an electrically conductive tip. In one exemplary embodiment of the present disclosure, the step 207 of measuring at least one current distribution of the testing sites with the electrical sensor 31 through the conductor 33 can be accomplished by measuring the current from the bias voltage 35, through the contact 23A, the mask article 20 and the conductor 33 to the electrical sensor 31. In a preferred embodiment of the present disclosure, the steps 205 and 207 can be implemented by contacting a first site 25A of the mask article 20 with the conductor 33, measuring a first current value passing through the first site 25A of the mask article 20 with the electrical sensor 31, moving the conductor 33 to contact a second site 25B of the mask article 20, measuring a second current value passing through the second site of the mask article 20 with the electrical sensor 33 and so on.

Figure 26:
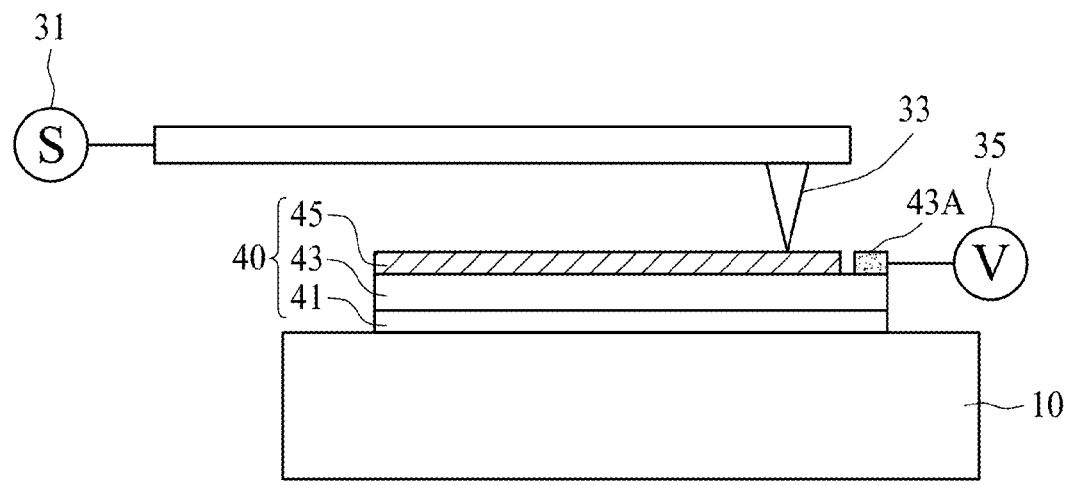
FIG. 26 is schematic diagram illustrating the testing of a mask article according to another embodiment of the present disclosure.

FIG. 26 is a schematic diagram illustrating the testing of a mask article 40 according to another embodiment of the present disclosure. In an exemplary embodiment of the present disclosure, the mask article 40 is a mask blank comprising a substrate 41 such as a quartz substrate, a conductive layer 43 such as a chromium layer, and a dielectric layer 45 such as a chromium oxide layer. In one embodiment of the present disclosure, the step 201 of applying a bias voltage 35 to the mask article 40 can be accomplished by forming at least one contact 43A on the conductive layer 43 of the mask article 40 and contacting a power probe of a bias voltage 35 such as a voltage source with the at least one contact 43A of the conductive layer 43. In another exemplary embodiment of the present disclosure, the step 201 of applying a bias voltage 35 to the mask article 40 can be accomplished by placing the mask article 40 on a stage 10 electrically connected to the bias voltage 35, and forming an electrical connection between the mask article 40 and the stage 10, as shown in FIG. 25.

Figure 27:
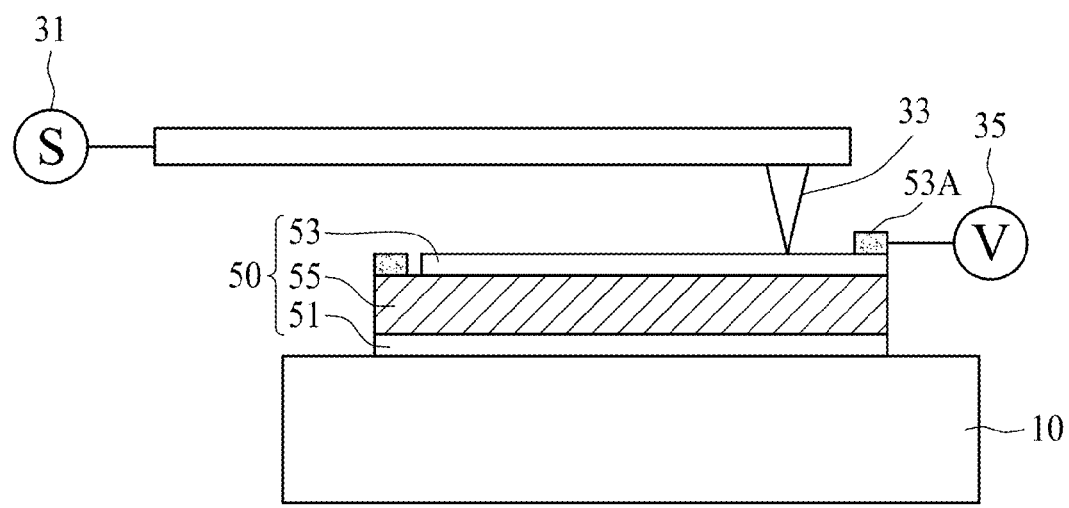
FIG. 27 and FIG. 28 are schematic diagrams illustrating the testing of a mask article with a multi-layer structure according to another embodiment of the present disclosure.
Figure 28:
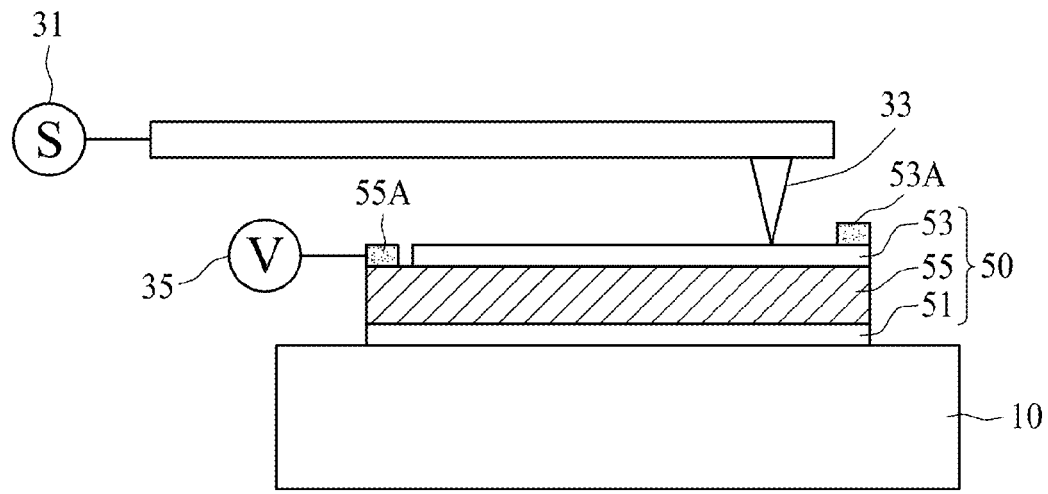

FIG. 27 and FIG. 28 are schematic diagrams illustrating the testing of a mask article 50 with a multi-layer structure according to another embodiment of the present disclosure. In an exemplary embodiment of the present disclosure, the mask article 50 is a mask blank comprising a substrate 51 such as a quartz substrate, a first layer 53 with at least one first contact 53A and a second layer 55 with at least one second contact 55A. In a preferred embodiment of the present disclosure, as shown in FIG. 27, the testing method of the mask article 50 comprises the steps of applying the bias voltage 35 to the first contact 53A, contacting the plurality of testing sites of the first layer 53 with the conductor 33, measuring a first current distribution of the first layer 53 with the electrical sensor 31; subsequently, as shown in FIG. 28, the testing method of the mask article 50 performs the steps of applying the bias voltage 35 to the second contact 55A, contacting the plurality of testing sites of the first layer 53 with the conductor 33, and measuring a second current distribution of the second layer 55 with the electrical sensor 31.

In an exemplary embodiment of the present disclosure, the testing method of the mask article 50 determines the quality of the mask article 50 by taking the first current distribution and the second current distribution into consideration. In another exemplary embodiment of the present disclosure, the step 201 of applying a bias voltage 35 to the mask article 50 can be accomplished by placing the mask article 50 on a stage 10 electrically connected to the bias voltage 35, and forming an electrical connection between the mask article 50 and the stage 10, as shown in FIG. 25.

Figure 29:
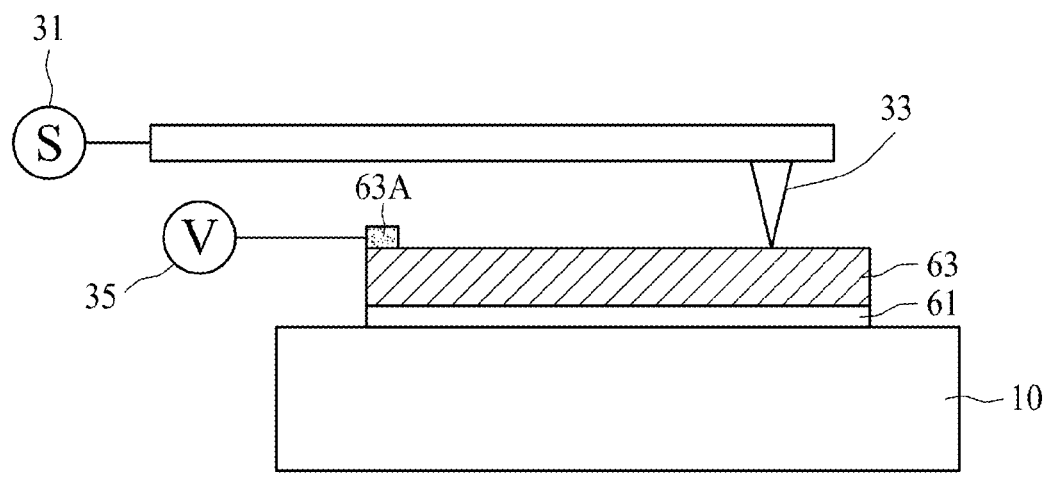
FIG. 29 and FIG. 30 are schematic diagrams illustrating the testing of a mask article with a multi-layer structure according to another embodiment of the present disclosure.
Figure 30:
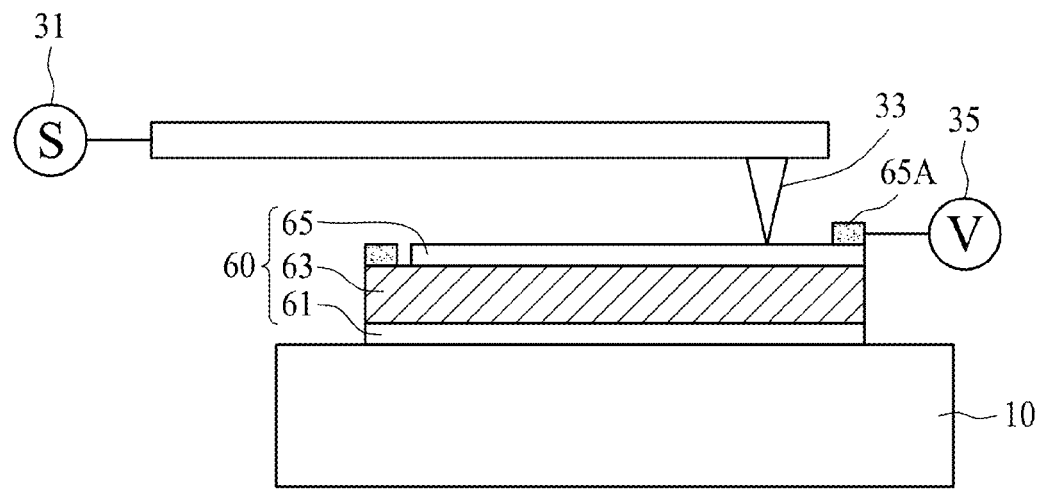

FIG. 29 and FIG. 30 are schematic diagrams illustrating the testing of a mask article 60 with a multi-layer structure according to another embodiment of the present disclosure. In one embodiment of the present disclosure, the testing method of the mask article 60 comprises the steps of forming a first layer 63 with at least one first contact 63A, applying the bias voltage 35 to the first contact 63A, contacting the first layer 63 with the conductor 33, measuring a first current distribution of the first layer 63 with the electrical sensor 31, as shown in FIG. 29. Subsequently, the testing method of the mask article 60 performs the steps of forming a second layer 65 with at least one second contact 65A, applying the bias voltage 35 to the second contact 65A, contacting the second layer 65 with the conductor 33, and measuring a second current distribution of the second layer 65 with the electrical sensor 31.

In one embodiment of the present disclosure, the testing method of the mask article 60 determines the quality of the mask article 60 by taking the first current distribution and the second current distribution into consideration. In another exemplary embodiment of the present disclosure, the step 201 of applying a bias voltage 35 to the mask article 60 can be accomplished by placing the mask article 60 on a stage 10 electrically connected to the bias voltage 35 and forming an electrical connection between the mask article 60 and the stage 10, as shown in FIG. 25.

Figure 31:
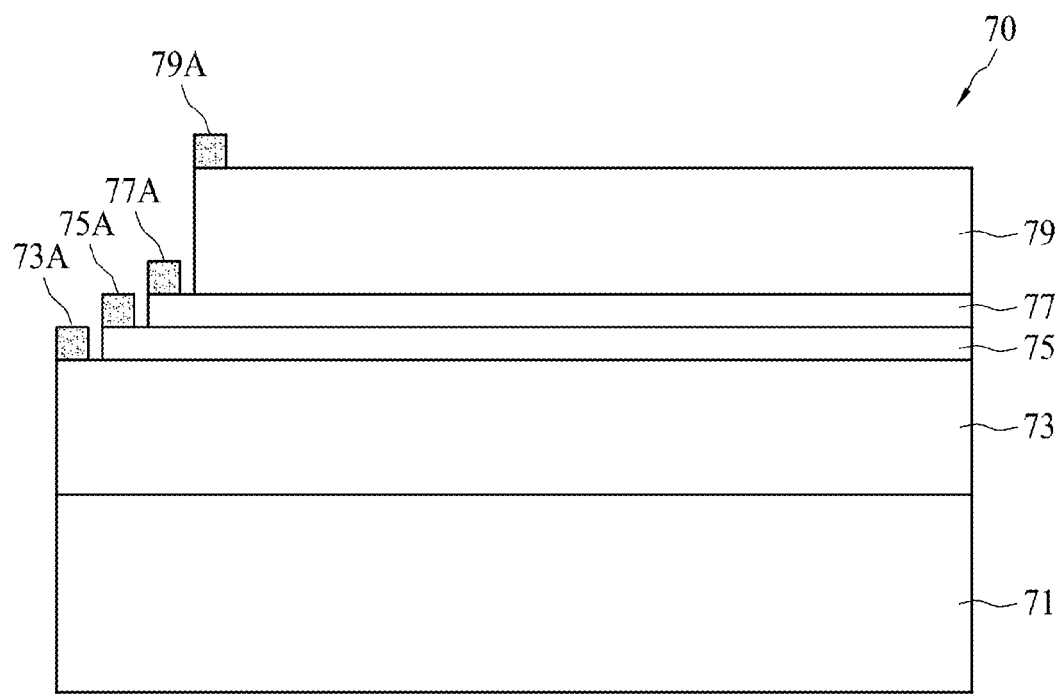
FIG. 31 and FIG. 32 are cross-sectional diagrams of a mask blank with a multi-layer structure, and the testing method of the present disclosure can be applied to the mask blank.
Figure 32:
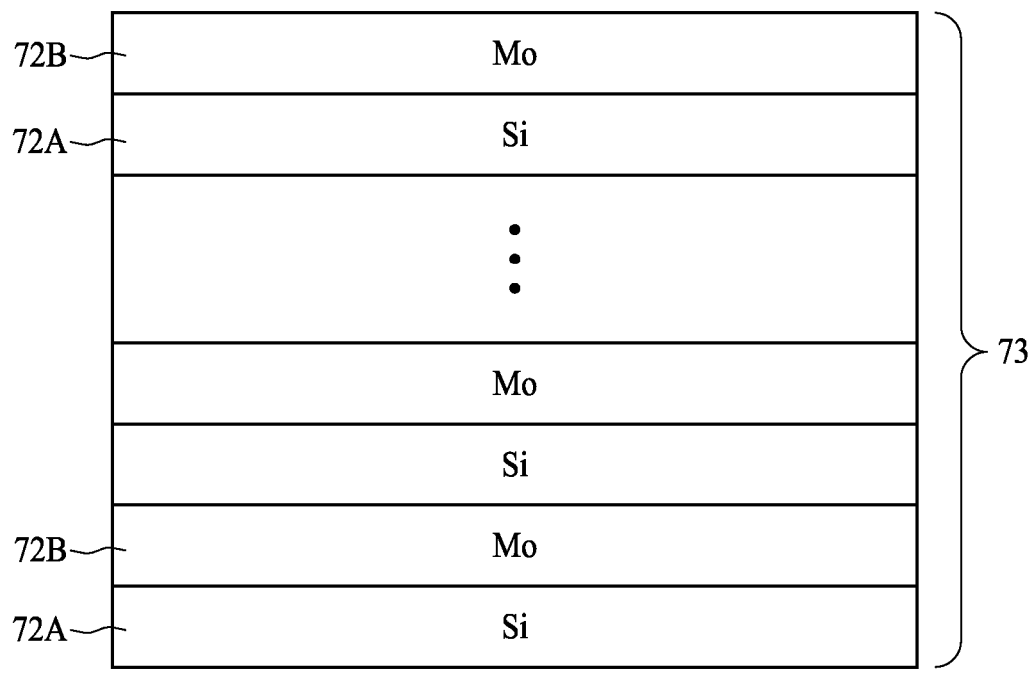

FIG. 31 and FIG. 32 are cross-sectional diagrams of a mask blank 70 with a multi-layer structure, and the testing method of the present disclosure can be applied to the mask blank 70. The mask blank 70 comprises a substrate 71, a reflective multi-layer 73, a capping (protecting) layer 75 including silicon, a buffer layer 77 including chromium and/or chromium nitride, and an absorber layer 79 including titanium nitride. In an exemplary embodiment of the present disclosure, the mask blank 70 is formed with at least one contact for each layer, i.e., at least one contact 73A is formed on the reflective multi-layer 73, at least one contact 75A is formed on the capping layer 75, at least one contact 77A is formed on the buffer layer 77, and at least one contact 79A is formed on the is absorber layer 79. In a preferred embodiment of the present disclosure, the contacts are formed on some of the layers, rather than formed on each layer.

In one embodiment of the present disclosure, the substrate 71 is a quartz substrate or a Ti-doped silicon oxide glass substrate. In one embodiment of the present disclosure, the reflective multi-layer 73 includes a Si layer 72A and a Mo layer 72B stacked in an alternating manner. However, the reflective multi-layer 73 is not limited thereto, but a Ru/Si multilayered reflective film, a Mo/Be multilayered reflective film, a Mo compound/Si compound multilayered reflective film, a Si/Mo/Ru multilayered reflective film, a Si/Mo/Ru/Mo multilayered reflective film or a Si/Ru/Mo/Ru multilayered reflective film may be employed.

In one embodiment of the present disclosure, as the layers of the mask blank 70 are formed with at least one contact, the testing method described in FIGS. 19-20 or FIGS. 27-28 can be applied to test the mask blank 70 after the fabrication process is completed. In another embodiment of the present disclosure, as the layers of the mask blank 70 are formed with at least one contact during the fabrication process of the mask blank 70, the testing method described in FIGS. 21-22 or FIGS. 29-30 can be applied to test the mask blank 70 during the fabrication process.

Figure 33:
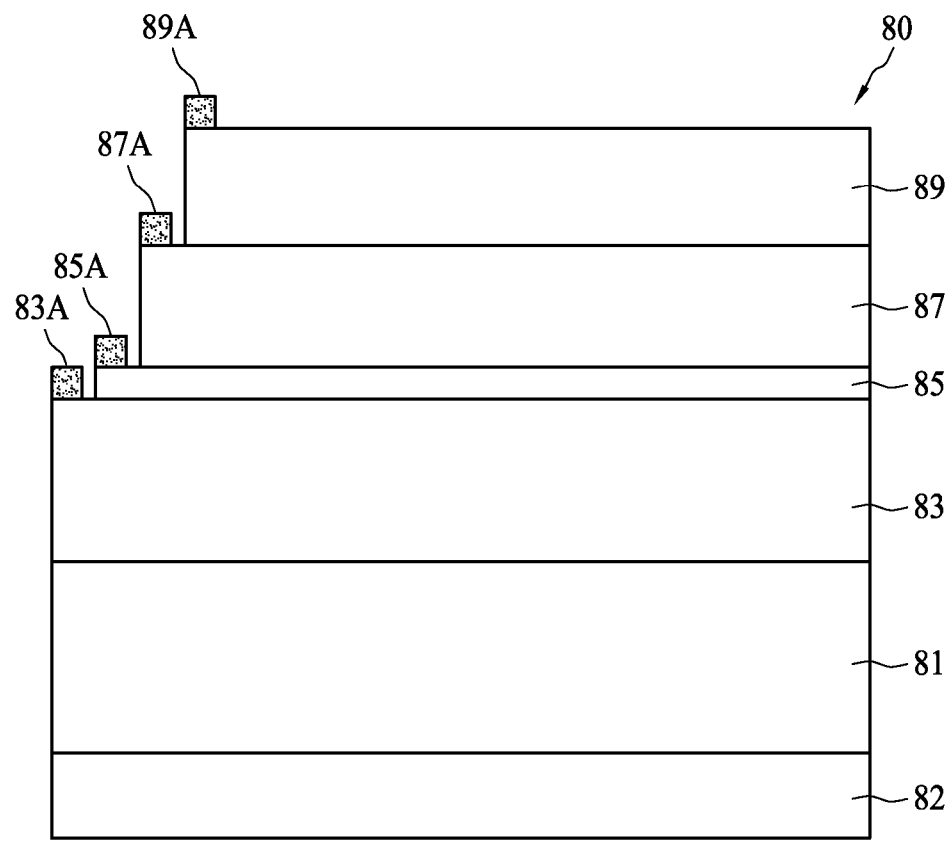
FIG. 33 is cross-sectional diagram of a mask blank with a multi-layer structure, and the testing method of the present disclosure can be applied to the mask blank.

FIG. 33 is cross-sectional diagram of a mask blank 80 with a multi-layer structure, and the testing method of the present disclosure can be applied to the mask blank 80. The mask blank 80 comprises a substrate 81, a backside layer 82 to such as a conductive layer including chromium, a reflective multi-layer 83 including Mo and Si layers stacked in an alternating manner as that shown in FIG. 32, a buffer (protecting) layer 85 including chromium or chromium nitride, an absorber layer 87 including titanium nitride, and a resist layer 89. In an exemplary embodiment of the present disclosure, the mask blank 80 is formed with at least one contact for each layer, i.e., at least one contact 83A is formed on the reflective multi-layer 83, at least one contact 85A is formed on the buffer layer 85, at least one contact 87A is formed on the absorber layer 87, and at least one contact 89A is formed on the resist layer 89. In one embodiment of the present disclosure, the substrate 81 is a quartz substrate or a Ti-doped silicon oxide glass substrate. In a preferred embodiment of the present disclosure, the contacts are formed on some of the layers, rather than formed on each layer.

In one embodiment of the present disclosure, as the layers of the mask blank 80 are formed with at least one contact, the testing method described in FIGS. 19-20 or FIGS. 27-28 can be applied to test the mask blank 80 after the fabrication process is completed. In another embodiment of the present disclosure, as the layers of the mask blank 80 are formed with at least one contact during the fabrication process of the mask blank 80, the testing method described in FIGS. 21-22 or FIGS. 29-30 can be applied to test the mask blank 80 during the fabrication process.

Figure 34:
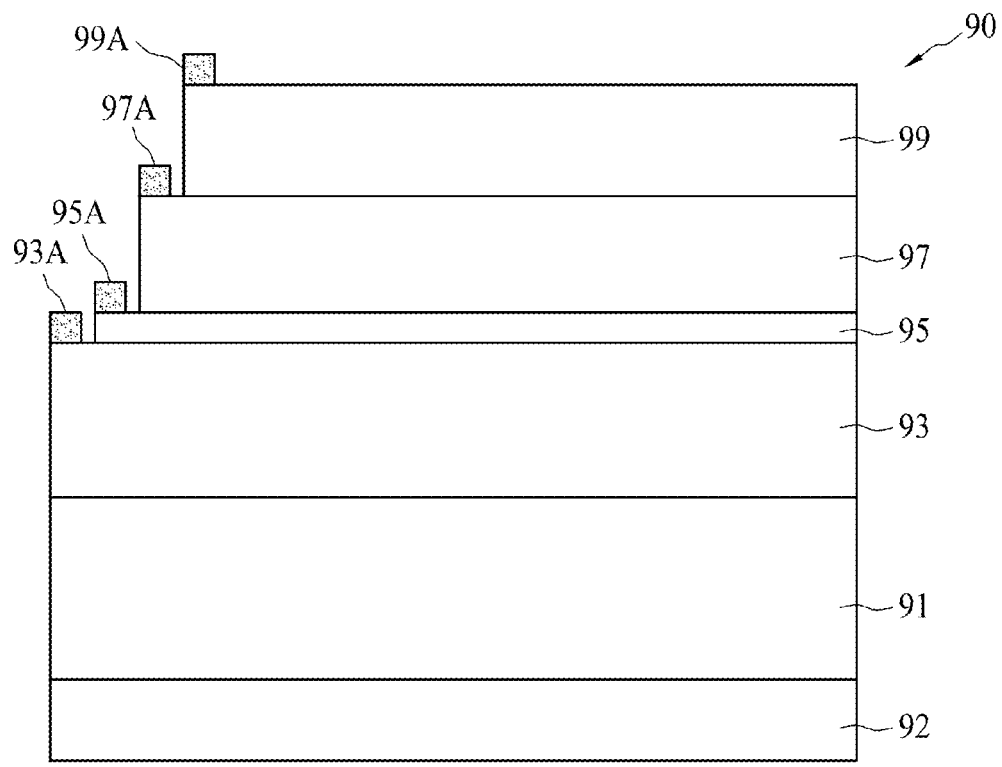
FIG. 34 is cross-sectional diagram of a mask blank with a multi-layer structure, and the testing method of the present disclosure can be applied to the mask blank.

FIG. 34 is a cross-sectional diagram of a mask blank 90 with a multi-layer structure, and the testing method of the present disclosure can be applied to the mask blank 90. The mask blank 90 comprises a substrate 91, a backside layer 92 such as a conductive layer including chromium, a reflective multi-layer 93 including Mo and Si layers stacked in an alternating manner, a capping (protecting) layer 95 including ruthenium, an absorber layer 97 including titanium nitride, and a resist layer 99. In an exemplary embodiment of the present disclosure, the mask blank 90 is formed with at least one contact for each layer, i.e., at least one contact 93A is formed on the reflective multi-layer 93, at least one contact 95A is formed on the capping layer 95, at least one contact 97A is formed on the absorber layer 97, and at least one contact 99A is formed on the resist layer 99. In one embodiment of the present disclosure, the substrate 91 is a quartz substrate or a Ti-doped silicon oxide glass substrate. In a preferred embodiment of the present disclosure, the contacts are formed on some of the layers, rather than formed on each layer.

In one embodiment of the present disclosure, as the layers of the mask blank 90 are formed with at least one contact, the testing method described in FIGS. 19-20 or FIGS. 27-28 can be applied to test the mask blank 90 after the fabrication process is completed. In another embodiment of the present disclosure, as the layers of the mask blank 90 are formed with at least one contact during the fabrication process of the mask blank 90, the testing method described in FIGS. 21-22 or FIGS. 29-30 can be applied to test the mask blank 90 during the fabrication process.

Figure 35:
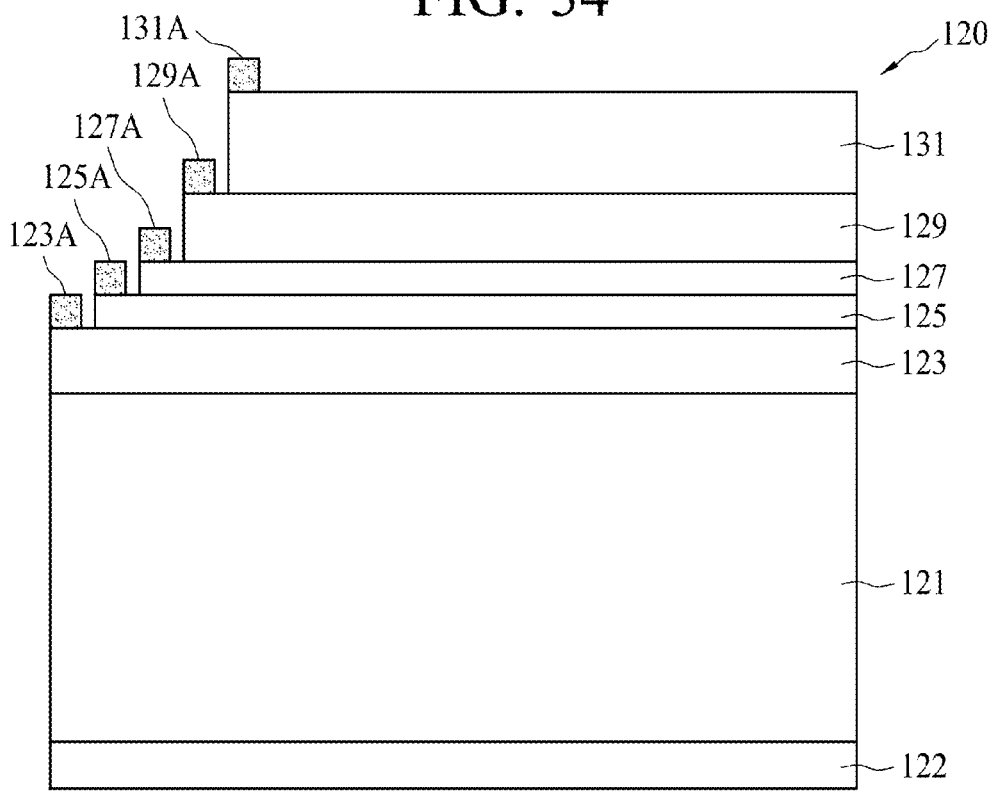
FIG. 35 is cross-sectional diagram of a mask blank with a multi-layer structure, and the testing method of the present disclosure can be applied to the mask blank.

FIG. 35 is a cross-sectional diagram of a mask blank 120 with a multi-layer structure, and the testing method of the present disclosure can be applied to the mask blank 120. The mask blank 120 comprises a substrate 121, a backside layer 122 such as a conductive layer including chromium, a reflective multi-layer 123 including Mo and Si layers stacked in an alternating manner, a capping (protecting) layer 125 including silicon, a buffer layer 127 including chromium nitride, an absorber layer 129 including titanium nitride, and a resist layer 131. In an exemplary embodiment of the present disclosure, the mask blank 120 is formed with at least one contact for each layer, i.e., at least one contact 123A is formed on the reflective multi-layer 123, at least one contact 125A is formed on the capping layer 125, at least one contact 127A is formed on the buffer layer 127, and at least one contact 129A is formed on the resist layer 129. In one embodiment of the present disclosure, the substrate 121 is a quartz substrate or a Ti-doped silicon oxide glass substrate. In a preferred embodiment is of the present disclosure, the contacts are formed on some of the layers, rather than formed on each layer.

In one embodiment of the present disclosure, as the layers of the mask blank 120 can be formed with at least one contact, the testing method described in FIGS. 19-20 or FIGS. 27-28 can be applied to test the mask blank 120 after the fabrication process is completed. In another embodiment of the present disclosure, as the layers of the mask blank 120 can be formed with at least one contact during the fabrication process of the mask blank 120, the testing method described in FIGS. 21-22 or FIGS. 29-30 can be applied to test the mask blank 120 during the fabrication process.

Figure 36:
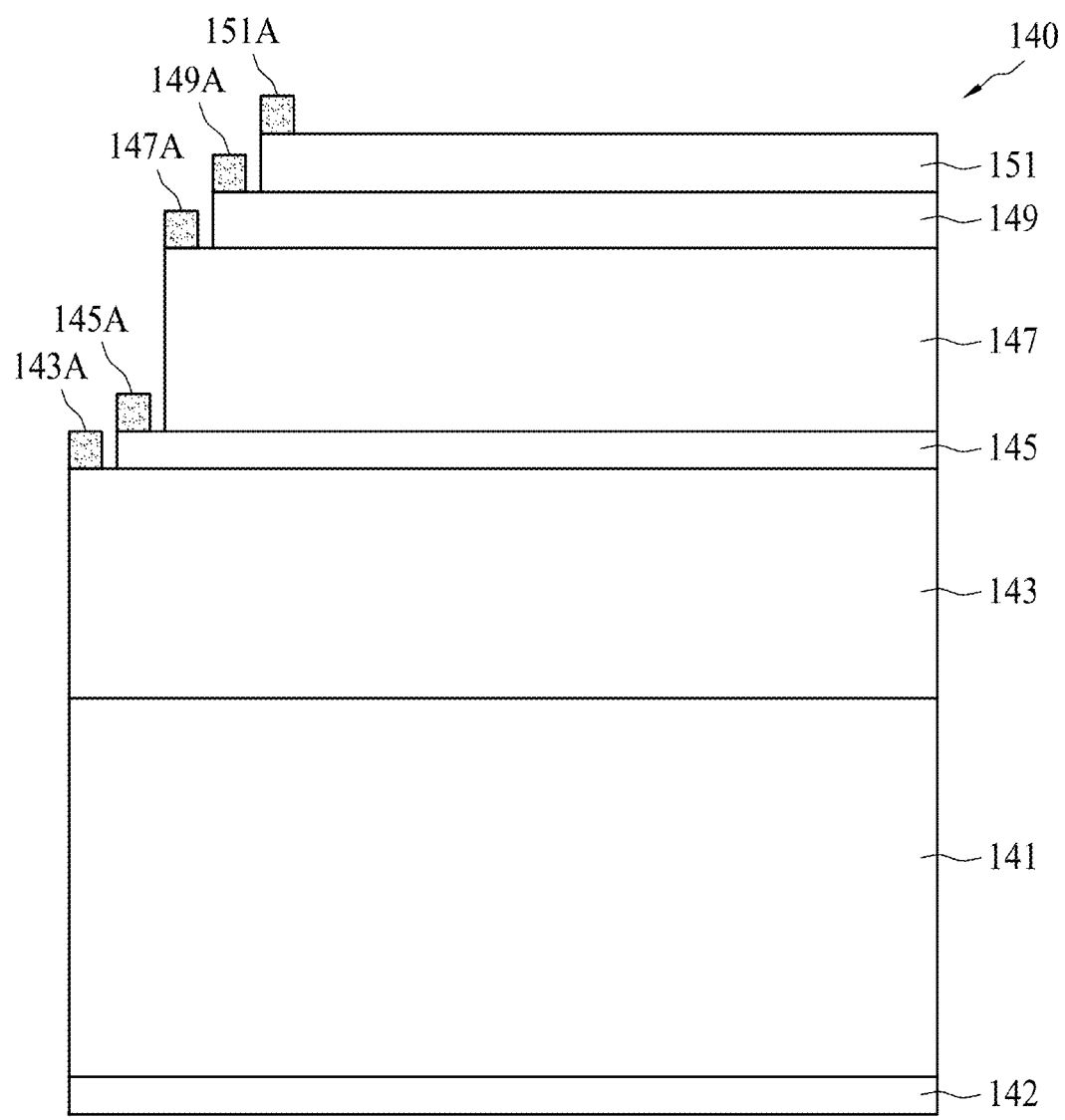
FIG. 36 is cross-sectional diagram of a mask blank with a multi-layer structure, and the testing method of the present disclosure can be applied to the mask blank.

FIG. 36 is a cross-sectional diagram of a mask blank 140 with a multi-layer structure, and the testing method of the present disclosure can be applied to the mask blank 140. The mask blank 140 comprises a substrate 141, a backside layer 142 such as a conductive layer including chromium or chromium nitride for electrostatic chuck, a reflective multi-layer 143 including Mo and Si layers stacked in an alternating manner, a capping/buffer (protecting) layer 145, an absorber layer 147, an anti-reflection layer 149, and a resist layer 151. In one embodiment of the present disclosure, the substrate 141 is a quartz substrate or a Ti-doped silicon oxide glass substrate; the absorber layer 147 includes material selected from the group consisting of tantalum nitride, tantalum silicon nitride, silicon oxide, tantalum, chromium nitride, tungsten, ruthenium and the combination thereof; the anti-reflection layer 149 includes material selected from the group consisting of silicon oxide, silicon nitride, aluminum oxide, silicon oxynitride and the combination thereof. The capping/buffer layer 145 includes material selected from the group consisting of carbon, carbon carbide, ruthenium, silicon nitride and a mixture thereof. Furthermore, the capping/buffer layer 145 is may include Cr, Al and Ta, a nitride thereof, Ru, a Ru compound (RuB, RuSi etc.), $SiO_2$, $Si_3N_4$, $Al_2O_3$ and a mixture thereof. Among these, it is preferred to use Ru, a Ru compound (RuB, RuSi etc.), and at least one of CrN and $SiO_2$, it is particularly preferred to use Ru or a Ru compound (RuB, RuSi etc.).

In an exemplary embodiment of the present disclosure, the mask blank 140 is formed with at least one contact for each layer, i.e., at least one contact 143A is formed on the reflective multi-layer 143, at least one contact 145A is formed on the capping/buffer layer 145, at least one contact 147A is formed on the absorber layer 147, at least one contact 149A is formed on the anti-reflection layer 149, and at least one contact 151A is formed on the resist layer 151. In a preferred embodiment of the present disclosure, the contacts are formed on some of the layers, rather than formed on each layer. In one embodiment of the present disclosure, the layers of the mask blank 140 can be formed with at least one contact for some interesting layers during the fabrication process of the mask blank 140, and the testing method described in FIGS. 19-20 or FIGS. 27-28 can be applied to test the mask blank 140 after the fabrication process is completed. In another embodiment of the present disclosure, the layers of the mask blank 140 can be formed with at least one contact for some interesting layers during the fabrication process of the mask blank 140, and the testing method described in FIGS. 21-22 or FIGS. 29-30 can be applied to test the mask blank 140 during the fabrication process. In preferred embodiment of the present disclosure, the layers of the mask blank 140 are formed with at least one contact for each layer.

Although the present disclosure and its advantages have been described in detail, it should be understood that various changes, substitutions and alterations can be made herein without departing from the spirit and scope of the disclosure as defined by the appended claims. For example, many of the processes discussed above can be implemented in different methodologies and replaced by other processes, or a combination thereof.

Moreover, the scope of the present application is not intended to be limited to the particular embodiments of the process, machines, manufacture, compositions of matter, means, methods and steps described in the specification. As one of ordinary skill in the art will readily appreciate from the disclosure of the present disclosure, processes, machines, manufacture, compositions of matter, means, methods, or steps presently existing or later to be developed, that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A method for testing a mask article, comprising steps of:
   applying a bias voltage to the mask article, wherein the mask article includes a conductive layer, and the bias voltage is applied to the conductive layer;
   electrically connecting a conductor to an electrical sensor;
   contacting a plurality of testing sites of the mask article with the conductor;
   measuring at least one current distribution of the testing sites with the electrical sensor through the conductor; and
   determining the quality of the mask article by taking the at least one current distribution into consideration, wherein the determining of the quality of the mask article includes a step of counting a number of testing sites with a current value lower than a threshold value.

2. The method for testing a mask article of claim 1, comprising steps of:
   contacting a first site of the mask article with the conductor;
   measuring a first current value passing through the mask article with the electrical sensor;
   contacting a second site of the mask article with the conductor; and measuring a second current value passing through the mask article with the electrical sensor.

3. The method for testing a mask article of claim 1, wherein the step of applying a bias voltage to the mask article comprises:
   forming at least one contact on the mask article; and
   contacting a power probe with the at least one contact.

4. The method for testing a mask article of claim 1, wherein the step of applying a bias voltage to the mask article is performed by placing the mask article on a stage electrically connected to a power source.

5. The method for testing a mask article of claim 1, wherein the mask article includes a first layer with a first contact and a second layer with a second contact, the method comprising steps of:
   applying the bias voltage to the first contact;
   contacting the first layer with the conductor;
   measuring a first current distribution of the first layer with the electrical sensor;
   applying the bias voltage to the second contact;
   contacting the first layer with the conductor; and
   measuring a second current distribution of the second layer with the electrical sensor.

6. The method for testing a mask article of claim 5, wherein the determining of the quality of the mask article is performed by taking the first current distribution and the second current distribution into consideration.

7. The method for testing a mask article of claim 1, comprising steps of:
   forming a first layer with at least one first contact;
   applying the bias voltage to the first contact;
   contacting the first layer with the conductor;
   measuring a first current distribution of the first layer with the electrical sensor;
   forming a second layer with at least one second contact;
   applying the bias voltage to the second contact;
   contacting the second layer with the conductor; and
   measuring a second current distribution of the second layer with the electrical sensor.

8. The method for testing a mask article of claim 7, wherein the determining of the quality of the mask article is performed by taking the first current distribution and the second current distribution into consideration.

9. A method for testing a mask article, comprising steps of:
   applying a bias voltage to the mask article, wherein the mask article includes a dielectric layer on a conductive layer, and the bias voltage is applied to the conductive layer;
   electrically connecting a conductor to an electrical sensor;
   contacting a plurality of testing sites of the mask article with the conductor;
   measuring at least one current distribution of the testing sites with the electrical sensor through the conductor; and
   determining the quality of the mask article by taking the at least one current distribution into consideration, wherein the determining of the quality of the mask article includes a step of counting a number of testing sites with a current value higher than a threshold value.

10. The method for testing a mask article of claim 9, comprising steps of:
   contacting a first site of the mask article with the conductor;
   measuring a first current value passing through the mask article with the electrical sensor;
   contacting a second site of the mask article with the conductor; and
   measuring a second current value passing through the mask article with the electrical sensor.

11. The method for testing a mask article of claim 9, wherein the step of applying a bias voltage to the mask article comprises:
   forming at least one contact on the mask article; and
   contacting a power probe with the at least one contact.

12. The method for testing a mask article of claim 9, wherein the step of applying a bias voltage to the mask article is performed by placing the mask article on a stage electrically connected to a power source.

13. The method for testing a mask article of claim 9, wherein the mask article includes a first layer with a first contact and a second layer with a second contact, the method comprising steps of:
   applying the bias voltage to the first contact;
   contacting the first layer with the conductor;
   measuring a first current distribution of the first layer with the electrical sensor;
   applying the bias voltage to the second contact;
   contacting the first layer with the conductor; and
   measuring a second current distribution of the second layer with the electrical sensor.

14. The method for testing a mask article of claim 13, wherein the determining of the quality of the mask article is performed by taking the first current distribution and the second current distribution into consideration.

15. The method for testing a mask article of claim 9, comprising steps of:
   forming a first layer with at least one first contact;
   applying the bias voltage to the first contact;
   contacting the first layer with the conductor;
   measuring a first current distribution of the first layer with the electrical sensor;
   forming a second layer with at least one second contact;
   applying the bias voltage to the second contact;
   contacting the second layer with the conductor; and
   measuring a second current distribution of the second layer with the electrical sensor.

16. The method for testing a mask article of claim 15, wherein the determining of the quality of the mask article is performed by taking the first current distribution and the second current distribution into consideration.

17. A method for testing a mask article, comprising steps of:
   applying a bias voltage to the mask article;
   electrically connecting a conductor to an electrical sensor;
   contacting a plurality of testing sites of the mask article with the conductor;
   measuring at least one current distribution of the testing sites with the electrical sensor through the conductor;
   determining the quality of the mask article by taking the at least one current distribution into consideration, wherein the determining of the quality of the mask article includes a step of calculating an average current of the testing sites.

18. The method for testing a mask article of claim 17, wherein the mask article includes a conductive layer, and the bias voltage is applied to the conductive layer.

19. The method for testing a mask article of claim 17, comprising steps of:
   contacting a first site of the mask article with the conductor;
   measuring a first current value passing through the mask article with the electrical sensor;
   contacting a second site of the mask article with the conductor; and measuring a second current value passing through the mask article with the electrical sensor.

20. The method for testing a mask article of claim 17, wherein the step of applying a bias voltage to the mask article comprises:
   forming at least one contact on the mask article; and
   contacting a power probe with the at least one contact.

21. The method for testing a mask article of claim 17, wherein the step of applying a bias voltage to the mask article is performed by placing the mask article on a stage electrically connected to a power source.

22. The method for testing a mask article of claim 17, wherein the mask article includes a first layer with a first contact and a second layer with a second contact, the method comprising steps of:
   applying the bias voltage to the first contact;
   contacting the first layer with the conductor;
   measuring a first current distribution of the first layer with the electrical sensor;
   applying the bias voltage to the second contact;
   contacting the first layer with the conductor; and
   measuring a second current distribution of the second layer with the electrical sensor.

23. The method for testing a mask article of claim 22, wherein the determining of the quality of the mask article is performed by taking the first current distribution and the second current distribution into consideration.

24. The method for testing a mask article of claim 17, comprising steps of:
   forming a first layer with at least one first contact;
   applying the bias voltage to the first contact;
   contacting the first layer with the conductor;
   measuring a first current distribution of the first layer with the electrical sensor;
   forming a second layer with at least one second contact;
   applying the bias voltage to the second contact;
   contacting the second layer with the conductor; and
   measuring a second current distribution of the second layer with the electrical sensor.

25. The method for testing a mask article of claim 24, wherein the determining of the quality of the mask article is performed by taking the first current distribution and the second current distribution into consideration.

* * * * *